US012575801B2

(12) United States Patent
Slomka et al.

(10) Patent No.: US 12,575,801 B2
(45) Date of Patent: Mar. 17, 2026

(54) EXPLAINABLE DEEP LEARNING CAMERA-AGNOSTIC DIAGNOSIS OF OBSTRUCTIVE CORONARY ARTERY DISEASE

(71) Applicant: CEDARS-SINAI MEDICAL CENTER, Los Angeles, CA (US)

(72) Inventors: Piotr Slomka, Los Angeles, CA (US); Ananya Singh, Los Angeles, CA (US); Paul Kavanagh, Santa Monica, CA (US); Sebastien Cadet, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 292 days.

(21) Appl. No.: 18/023,092

(22) PCT Filed: Aug. 27, 2021

(86) PCT No.: PCT/US2021/047976
§ 371 (c)(1),
(2) Date: Feb. 24, 2023

(87) PCT Pub. No.: WO2022/047173
PCT Pub. Date: Mar. 3, 2022

(65) Prior Publication Data
US 2023/0309940 A1 Oct. 5, 2023

Related U.S. Application Data

(60) Provisional application No. 63/216,903, filed on Jun. 30, 2021, provisional application No. 63/071,841, filed on Aug. 28, 2020.

(51) Int. Cl.
A61B 6/50 (2024.01)
A61B 6/00 (2006.01)
A61B 6/03 (2006.01)

(52) U.S. Cl.
CPC ............ *A61B 6/503* (2013.01); *A61B 6/5217* (2013.01); *A61B 6/037* (2013.01)

(58) Field of Classification Search
CPC ......... A61B 6/037; A61B 6/463; A61B 6/503; A61B 6/507; A61B 6/5217; G06V 10/82;
(Continued)

(56) References Cited

U.S. PATENT DOCUMENTS

2015/0112182 A1* 4/2015 Sharma ................ A61B 5/0261
600/408
2017/0262995 A1 9/2017 Li et al.
(Continued)

OTHER PUBLICATIONS

Betancur et al., "Deep Learning Analysis of Upright-Supine High-Efficiency SPECT Myocardial Perfusion Imaging for Prediction of Obstructive Coronary Artery Disease: A Multicenter Study", The Journal of Nuclear Medicine, vol. 60, No. 5,May 1, 2019), pp. 664-670, Retrieved from the Internet: URL:https://jnm.snmjournals.org/content/jnumed/60/5/664.full-text.pdf>.
(Continued)

*Primary Examiner* — Manuchehr Rahmjoo
(74) *Attorney, Agent, or Firm* — NIXON PEABODY LLP

(57) ABSTRACT

A deep learning model for the detection of obstructive coronary artery disease (CAD) can take a set of polar maps and patient information as input, then output obstructive CAD scoring data, such as probabilities of obstructive CAD associated with various cardiac territories, as well as an attention map and a CAD scoring map. The model can operate agnostic of camera type used to capture the set of polar maps. The attention map indicates regions of the polar maps important to the deep learning process for that particular set of polar maps. The attention map and obstructive CAD scoring data can be used to generate a CAD scoring map showing CAD probability by segment on a standard 17-segment model of a left ventricle. The attention map
(Continued)

and/or CAD scoring map can act as easily explainable tools for interpreting the results of a myocardial perfusion imaging study.

24 Claims, 16 Drawing Sheets

(58) Field of Classification Search
CPC ........ G06V 40/14; G16H 30/40; G16H 50/20; G16H 50/30
See application file for complete search history.

(56) References Cited

U.S. PATENT DOCUMENTS

| | | |
|---|---|---|
| 2018/0217162 A1 | 8/2018 | Fu et al. |
| 2020/0033615 A1* | 1/2020 | Kim ........................ G02B 30/40 |
| 2020/0134858 A1* | 4/2020 | Yang ..................... G06T 7/0004 |
| 2020/0205745 A1 | 7/2020 | Khosousi et al. |
| 2023/0138380 A1* | 5/2023 | Chen ................... G06F 18/2148 |
| | | 382/131 |

OTHER PUBLICATIONS

Otaki et al., "Clinical Deployment of Explainable Artificial Intelligence of SPECT for Diagnosis of Coronary Artery Disease", JACC: Cardiovascular Imaging, Elsevier, Amsterdam, NL; vol. 15, No. 6, Jun. 2022, pp. 1091-1102.
Slomka et al., "Fully automated wall motion and thickening scoring system for myocardial perfusion SPECT: method development and validation in large population", Journal of Nuclear Cardiology, Mosby, St. Louis, US, vol. 19, No. 2, Mar./Apr. 2012, pp. 291-302.
Extended European Search Report for EP Application No. 21862834.5 mailed Jul. 11, 2024, 11 pp.
ISR and WO for PCT/US2021/047976 mailed Dec. 6, 2021, 7 pages.

* cited by examiner

100
110
112
104
106
108
102
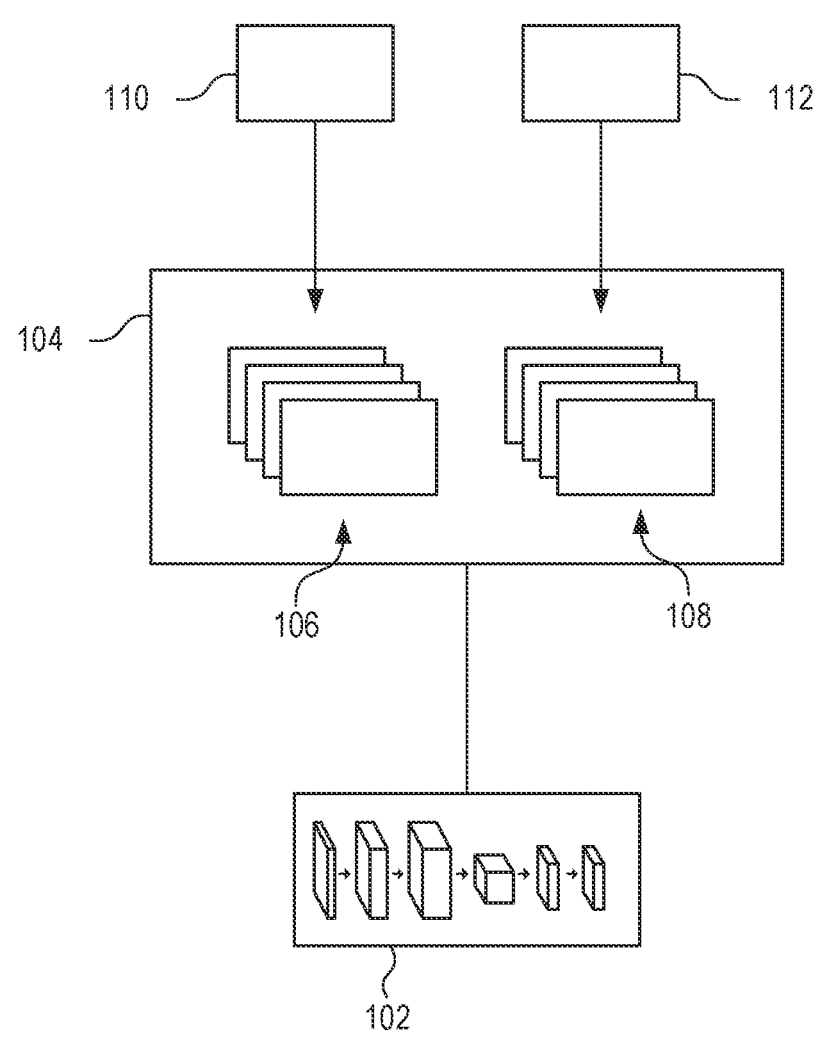
FIG. 1

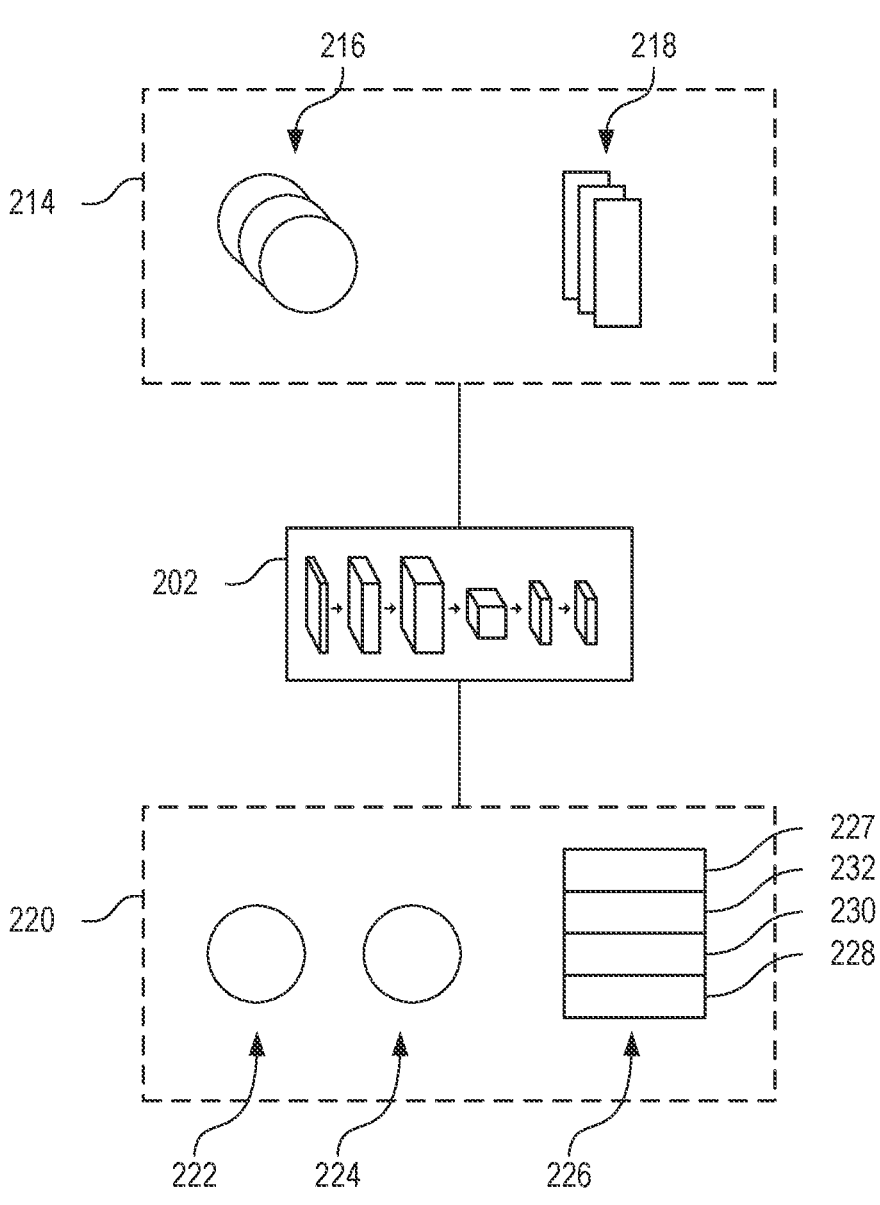
FIG. 2

1500

Receive input data associated with myocardial perfusion
imaging study
1502

Provide input data to a deep learning model
1504

Generate scoring
data for obstructive
coronary artery
disease
1506

Generate attention
map
1508

Generate coronary artery disease scoring map
1510

Present results from deep learning model
1512

Present scoring data
for obstructive
coronary artery
disease
1514

Present attention
map
1516

Present coronary
artery disease
scoring map
1518

FIG. 15

EXPLAINABLE DEEP LEARNING CAMERA-AGNOSTIC DIAGNOSIS OF OBSTRUCTIVE CORONARY ARTERY DISEASE

CROSS-REFERENCE TO RELATED APPLICATIONS

This application is a national phase of International Application No. PCT/US2021/047976, filed Aug. 27, 2021, which designated the U.S. and that International Application was published under PCT Article 21(2) in English. This application also claims the benefit of U.S. Provisional Patent Application No. 63/071,841 filed Aug. 28, 2020 and entitled "EXPLAINABLE DEEP LEARNING CAMERA-AGNOSTIC DIAGNOSIS OF OBSTRUCTIVE CORONARY ARTERY DISEASE" and U.S. Provisional Patent Application No. 63/216,903 filed Jun. 30, 2021 and entitled "EXPLAINABLE DEEP LEARNING CAMERA-AGNOSTIC DIAGNOSIS OF OBSTRUCTIVE CORONARY ARTERY DISEASE," both of which are hereby incorporated by reference in their entirety.

STATEMENT REGARDING FEDERALLY SPONSORED RESEARCH OR DEVELOPMENT

This invention was made with government support under Grant No. HL089765 awarded by National Institutes of Health. The government has certain rights in the invention.

TECHNICAL FIELD

The present disclosure relates to nuclear cardiology generally and more specifically to tools for obtaining and interpreting diagnostic information of obstructive disease.

BACKGROUND

Myocardial ischemia associated with obstructive disease (e.g., obstructive atherosclerotic coronary artery disease (CAD)) is a major cause of death. Accurate identification of obstructive disease is important. Accurate detection and diagnosis can be important to effectively avoiding or treating the disease. Myocardial perfusion imaging (MPI), also known as a nuclear stress test, is a type of test that can be used to diagnose obstructive disease.

MPI involves injecting a patient with a radioactive tracer that is absorbable into tissue of the heart. Regions with low-absorption of the tracer can be associated with inadequate perfusions, which may indicate obstructive disease. The amount of tracer absorbed into the heart tissue can be measured using a radioactive-sensitive detector, such as a single-photon emission computed tomography (SPECT) scanner. A SPECT scanner can utilize a camera that detects radiation emitted from a gamma-emitting radioactive tracer. The SPECT scanner generates images of the detected radiation and with reconstruction can it can provide a three-dimensional dataset of myocardial perfusion. This dataset can be further analyzed to identify obstructive disease.

A camera commonly used in SPECT scanners is a scintillation camera, commonly known as an Anger camera. The Anger camera makes use of vacuum tube photomultipliers for its measurements. Use of such a camera in SPECT imaging is generally associated with high radiation dose, longer acquisition times, and less optimal image quality, especially in women with increased breast tissue. A newer cadmium zinc telluride (CZT) based camera with solid state detectors has been recently introduced, which can improve diagnostic accuracy with reduced radiation and shorter acquisition time. However, differences between different camera types can increase the difficulty in accurately detecting obstructive disease from the scanner data. In some cases, separate models or separate camera-specific normal limits may be needed to accurately detect obstructive disease. Similar perfusion images can also be created with Positron Emission tomography (PET) scanners.

Some techniques for identifying obstructive disease involve calculating total perfusion deficit (TPD) values. Recently, it has been found that deep learning can be utilized to detect obstructive disease, however such deep learning techniques rely heavily on camera-specific and sex-specific databases of normal limits. Further, deep learning techniques are often frowned upon or discouraged because the end result is presented to the physician in a "black-box" fashion.

There is a need to be able to accurately detect obstructive disease in a camera-agnostic manner. There is also a need to provide information about obstructive disease detection in a easily viewable and explainable fashion.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a system comprising one or more data processors and a non-transitory computer-readable storage medium containing instructions which, when executed on the one or more data processors, cause the one or more data processors to perform operations of the method described below. Embodiments of the present disclosure include a computer-program product tangibly embodied in a non-transitory machine-readable storage medium, including instructions configured to cause a data processing apparatus to perform operations of the method described below.

Embodiments of the present disclosure include a computer-implemented method, comprising: receiving input data associated with a myocardial perfusion imaging study of a patient, wherein the input data comprises a set of polar maps and patient information, wherein the set of polar maps comprises a perfusion polar map, a motion polar map, and a thickening polar map, and wherein the patient information comprises at least one selected from the set consisting of sex information, age information, and cardiac volume information; providing the input data to a deep learning model, wherein the deep learning model comprises an input layer, at least one convolution layer, at least one pooling layer, and at least one fully connected layer; generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) a probability for obstructive CAD in a right coronary artery (RCA) territory, or v) any combination of i-iv; generating an attention map in response to providing the input data to the deep learning model, wherein the attention map is indicative of regions of importance associated with the obstructive CAD scoring data; presenting, on a display device, the obstructive CAD scoring data and the attention map, and the 17-segment American Heart Association map with segment colored according to the attention map.

In some cases, generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model. In some cases, the method (or operations) further comprise generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data. In some cases, the deep learning model was previously trained using training data collected using a plurality of camera types. In some cases, the deep learning model was previously trained using a first set of training data collected using a vacuum-tube-photomultiplier-based camera and a second set of training data collected using a cadmium-zinc-telluride-based camera. In some cases, providing the input data to the deep learning model comprises: providing the set of polar maps to the input layer of the deep learning model; and providing the patient information to the at least one fully connected layer of the deep learning model. In some cases, the at least one fully connected layer includes a fully connected output layer, and wherein providing the patient information to the at least one fully connected layer comprises providing the patient information to the fully connected output layer. In some cases, providing the set of polar maps to the deep learning model comprises providing the set of polar maps without pre-defined coronary territories.

BRIEF DESCRIPTION OF THE DRAWINGS

The specification makes reference to the following appended figures, in which use of like reference numerals in different figures is intended to illustrate like or analogous components.

FIG. 1 is a schematic diagram depicting a system for training a deep learning model for detecting obstructive coronary artery disease, according to certain aspects of the present disclosure.

FIG. 2 is a schematic diagram depicting a system for using a deep learning model for detecting obstructive coronary artery disease, according to certain aspects of the present disclosure.

FIG. 15 is a flowchart depicting a process for using a deep learning model for detecting obstructive coronary artery disease, according to certain aspects of the present disclosure.

DETAILED DESCRIPTION

Figure 3:
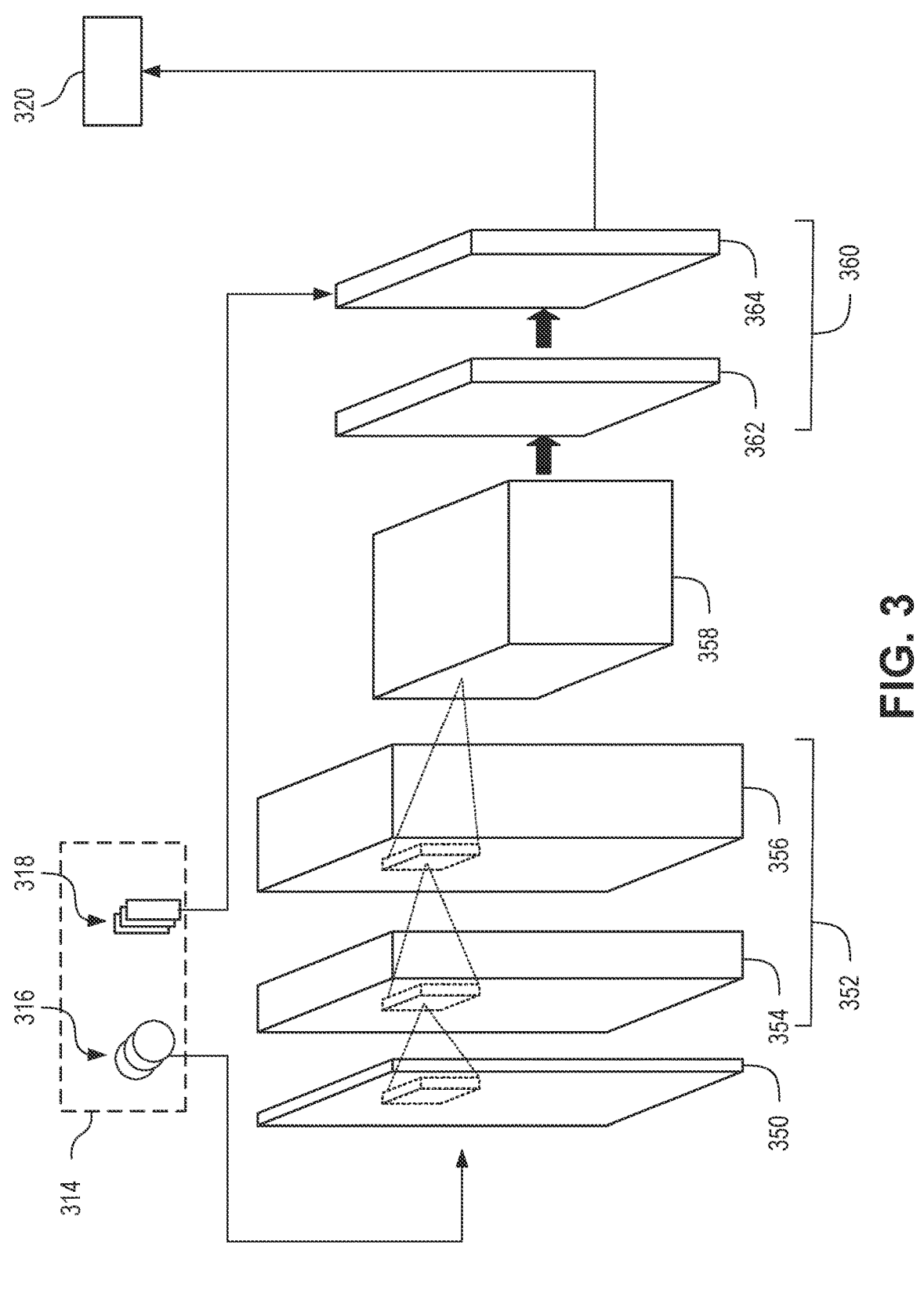
FIG. 3 is a schematic diagram of a deep learning model for detecting obstructive coronary artery disease, according to certain aspects of the present disclosure.

Certain aspects and features of the present disclosure relate to detection of obstructive coronary artery disease (CAD) using a deep learning model. The deep learning model can take a set of polar maps and patient information as input, then output an obstructive CAD scoring data (e.g., an overall probability of obstructive CAD and/or set of probabilities of obstructive CAD associated with various cardiac territories), as well as an attention map and a CAD scoring map. The deep learning model can operate agnostic of camera type used to capture the set of polar maps. The attention map can indicate regions of the polar maps which are important to the deep learning process for that particular set of polar maps. The attention map and obstructive CAD scoring data can be used to generate a CAD scoring map showing CAD probability (or other scoring data) by segment on a standard 17-segment model of a left ventricle. The attention map and/or CAD scoring map can act as easily explainable tools for interpreting the results of a myocardial perfusion imaging study. These explainable tools allow a physician, patient, or other individual the ability to better see and understand why the polar maps lead to the obstructive CAD scoring data that the trained deep learning model outputs.

A myocardial perfusion imaging (MPI) study can include the collection of information from a suitable scanner, such as a single-photon emission computed tomography (SPECT) scanner or Positron emission tomography (PET) scanner. Once the data associated with the MPI study is collected, however, it must be analyzed to provide a diagnostic benefit.

The input data from an MPI study can take any suitable form, such as a collection of polar maps representative of a patient's heart (e.g., a left ventricle of a patient's heart). Input data from an MPI study can include imaging data collected from a scanner (e.g., data making up a polar map) as well as supplemental data, such as patient information and/or metadata. In some cases, supplemental data can be stored alongside sensed data, such as metadata stored as part of imaging data using the Digital Imaging and Communications in Medicine (DICOM) standard.

In some cases, input data from an MPI study can include a set of polar maps including a perfusion polar map, a motion polar map, a thickening polar map, or any combination thereof. In some cases, input data can include raw gated and/or ungated polar maps, such as a raw polar map of ungated perfusion and gated maps of motion and thickening. In some cases, the polar maps can be input without the use of pre-defined coronary territories and/or any assumed subdivisions. In some cases, input data from an MPI study can further include age information and/or sex information of the patient. In some cases, input data from an MPI study can include cardiac volume information, such as an end-diastolic volume (EDV), an end-systolic volume (ESV), a stroke volume (SV), or any combination thereof. In some cases, the cardiac volume information used as input data can be that of the left ventricle, although that need not always be the case.

The input data can be provided to a deep learning model, as disclosed herein. The deep learning model can be a neural network, such as a convoluted neural network, that has been trained to accept input data from an MPI study and output desired outputs to facilitate diagnosing obstructive CAD. These desired outputs can include obstructive CAD scoring data. Obstructive CAD scoring data can be an indication of an intensity of or likelihood of obstructive CAD. In some cases, the obstructive CAD scoring data can be a global probability of obstructive CAD for a heart and/or a set of probabilities of CAD for certain territories of a heart, such as a probability of CAD in a left anterior descending (LAD) territory, a probability of CAD in a left circumflex artery (LCx) territory, a probability of CAD in a right coronary artery (RCA) territory, or any combination thereof. In some cases, obstructive CAD scoring data can be provided in forms other than probability data, such as a binary indication of the presence or absence of obstructive CAD for each of various territories of the heart. Where appropriate, reference to scoring data in the form of a probability or probabilities of CAD can be replaced with reference to other forms of scoring data. The desired outputs can also include an attention map and/or a CAD scoring map (e.g., a CAD probability map), as disclosed herein.

An attention map can be a polar map or an overlay on a polar map that indicates regions of the input polar map(s) that are important for determination of obstructive CAD. The attention map can easily and quickly highlight to a reader the regions contributing most to the per-vessel CAD predictions for a given patient. The attention map can provide insight to the decision-making process of the deep learning model by highlighting regions of importance. The attention map can be generated using gradient-weighted class activation mapping (Grad-CAM), such as the mapping techniques disclosed in "Grad-CAM: visual explanations from deep networks via gradient-based localization" (Selvaraju R R, et al., 2017 IEEE International Conference on Computer Vision (ICCV). 2017:618-26). Generation of the attention map can include using gradients of a predicted vessel flowing into the final convolutional layer to produce a coarse localization map that is the attention map. The output after the final convolution layer can be extracted using a Grad-CAM technique to access the importance of each neuron in the deep learning model prediction. The per-vessel CAD probabilities, or other CAD scoring data, can be backpropagated to the convolution layer where the target gradients are extracted. After applying global average pooling and ReLU (Rectified Linear Unit) activations, a coarse localization map can be obtained, which weights the regions of interest. The coarse localization map can be resized and overlaid on the raw polar map. As applicable, the term attention map can refer to the coarse localization map, the overlay, or the combination overlay and raw polar map. The attention map can highlight the important deep learning model decision making regions in the polar maps. The attention map can be indicative of an amount of information contribution each pixel of the polar map provides to the determined CAD probabilities or other CAD scoring data.

A CAD scoring map can be a segmented heart model (e.g., a standard 17-segment heart model) that is coded (e.g., color-coded) to indicate the CAD scoring data for each of the segments. In some cases, the CAD scoring map displays CAD probabilities for each of the segments, in which case the map may be known as a CAD probability map. The CAD scoring map can be a translation of the attention map into a segmented model to identify individual segments of interest. The CAD scoring map can be generated by segmenting the attention map and using the CAD scoring data (e.g., the set of probabilities of CAD) for certain territories of the heart to match the appropriate CAD scoring data (e.g., CAD probabilities) to each segment. In some cases, optionally for each segment that exceed a threshold value, the segment can be assigned to a severity category (e.g., severity of perfusion defect categorization).

In some cases, each segment can be assigned one of a set number of severity categories based on the per vessel predictions of CAD probability and the importance of the segment highlighted by the attention map. In some cases, the number of severity categories can be 5, although other numbers of categories can be used. The severity categories can range from a lowest category representing 0% probability of CAD to a highest category representing 100% probability of CAD. The CAD probability map can display per-vessel CAD probability and important segments highlighted by the attention map simultaneously. This CAD probability map flags the polar map segments with predicted severity defects for the reader, to visualize and give an insight to the deep learning model's rationale. The CAD probability map can easily and quickly highlight to a reader the segments contributing most to the per-vessel CAD predictions for a given patient. The CAD probability map can flag the segments with predicted severity defect for the reader, thus visualizing the risk prediction rationale for clinicians. Generation of the CAD probability map can occur relatively quickly, on the order of seconds or tens of seconds on a standard computing device. In some cases, other scoring data can be used instead of CAD probabilities.

In some cases, a deep learning model as disclosed herein can be trained to take as input raw perfusion, motion, and thickening polar maps collected in a supine position, along with patient information, such as age information, sex information, and/or cardiac volume information (e.g., left ventricular cardiac volume information). This deep learning model can output desired outputs to facilitate diagnosing obstructive CAD, as disclosed herein, such as a prediction of overall CAD probability for the heart, predictions of per vessel CAD probability for LAD, LCx, and RCA territories, or any combination thereof. Such a deep learning model can operate without the need for camera-specific and/or sex-specific normal limits for quantification maps. Imaging numerical features can be easily obtained from DICOM and polar map headers. In some cases, data from an additional upright or prone MPI study may be used.

Various deep learning models can be used with different inputs. Through nontrivial trial and experimentation, it has been determined that especially strong diagnostic performance can be achieved by including age information, sex information, and cardiac volume information (e.g., left ventricular cardiac volume information) along with the use of polar maps (e.g., raw perfusion, motion, and thickening polar maps). Table 1 depicts diagnostic performance (e.g., area under the receiver operating characteristic curve (AUC) with 95% confidence interval (CI)) for example deep learning models trained using different combinations of inputs. Of note, disease diagnosis was not improved by adding quantified perfusion data (e.g., total perfusion deficit (TPD)) to the model. Thus, the example of Model 6 is not dependent on normal perfusion databases or specific MPI software.

TABLE 1

| Model # and Inputs | AUC [95% CI] | P value compared to Model 1 | P value compared to Model 6 |
|---|---|---|---|
| Model 1: Polar maps only | 0.81 [0.80-0.83] | — | <0.0001 |
| Model 2: Polar maps + cardiac volume information | 0.81 [0.80-0.83] | 0.05 | <0.0001 |
| Model 3: Polar maps + sex information | 0.82 [0.81-0.83] | 0.0015 | 0.0003 |
| Model 4: Polar maps + sex information + age information | 0.82 [0.81-0.84] | 0.0012 | 0.0025 |
| Model 5: Total perfusion deficit + age information + sex information + cardiac volume information (no polar maps) | 0.80 [0.79-0.81] | 0.06 | <0.0001 |
| Model 6: Polar maps + age | 0.83 [0.82-0.85] | <0.0001 | — |

8

TABLE 1-continued

| Model # and Inputs | AUC [95% CI] | P value compared to Model 1 | P value compared to Model 6 |
|---|---|---|---|
| information + sex information + cardiac volume information | | | |

According to certain aspects and features of the present disclosures, extent and quantitative polar maps need not be utilized, thus removing the dependency on specific clinical software for quantitation and the need for camera-specific normal databases. Further, using the polar map format resolves variabilities in raw SPECT data between sites, camera types, tracers, and patients, which otherwise may have been identified during deep learning training as important features.

A deep learning model as disclosed herein can be trained using multi-camera, multi-side data. Multi-camera data can include data from Anger-camera-based SPECT scanners as well as data from CZT-based SPECT camera or PET camera. In some cases, the training data can be from solely supine MPI studies.

In some cases, a CZT-camera-based deep learning model can be trained using upright and supine MPI studies from CZT-camera-based MPI studies. This deep learning model can be trained similarly to the multi-camera deep learning model, but with the input polar maps being raw perfusion supine and upright polar maps.

A deep learning model as disclosed herein can be a deep neural network, such as a convolutional neural network. This convolutional neural network can be designed and trained to accept polar maps at an input layer, manipulate the input layer through a set of convolutional layers, manipulate the resultant signal(s) through a pooling layer, then manipulate the resultant signal(s) using one or more fully connected layers. The convolutional neural network can be designed and trained to accept supplemental patient information (e.g., age information, sex information, and cardiac volume information) at a fully connected layer, such as at a final fully connected layer. In some cases, the patient information (e.g., age, sex, and cardiac volumes) were normalized and concatenated to the final fully connected layer, resulting in a probability vector of obstructive per-vessel CAD prediction.

The deep learning model can be designed and trained to output the desired outputs (e.g., a set of per vessel CAD probabilities, an attention map, and a CAD scoring map). In some cases, the deep learning model can be designed and trained to output a set of per vessel CAD probabilities and an attention map, with a CAD scoring map being later generated in response to outputting of the set of per vessel CAD probabilities and the attention map.

The specific way the deep learning model is constructed and trained, as disclosed herein, including the selection of layers involved and the types of inputs provided, can result in an especially useful model for evaluating myocardial perfusion imaging studies and identifying possible obstructive CAD.

In use, certain aspects and features of the present disclosure can be implemented within or alongside standard clinical software and can generate results rapidly (e.g., in at or less than 12 seconds on a standard clinical workstation). Further, since the disclosed techniques can generate CAD scoring data using only limited clinical information, which is generally extractable from metadata associated with the image(s), this CAD scoring data can be generated without the need for additional physician effort (e.g., to manually find and enter input data), which can also reduce the chance of human error in entering data. Thus, in some cases, certain aspects of the present disclosure can operate without the need to manually collect additional clinical information other than what is included with the image(s).

Certain aspects and features of the present disclosure provide various improvements to the technological process of diagnosing obstructive CAD. Examples of such improvements include faster diagnosis, improved accuracy of CAD detection, much-improved explainability of the importance of different segments of the polar maps, ability to provide overall and per-territory CAD scoring data, and others. When implemented, certain aspects and features of the present disclosure can reduce the time it takes for an expert practitioner (e.g., medical doctor) to read and interpret each myocardial imaging study, which can reduce cost to patients, increase availability for the practitioner to interpret additional studies, and decrease the amount of elapsed time before the patient receives a diagnosis and subsequent treatment. In some examples, the generation and presentation of an attention map and/or obstructive CAD scoring data (e.g., one or more probabilities for obstructive CAD) via the disclosed trained deep learning model can enable these and other improvements.

While certain aspects and features of the present disclosure are described with reference to detecting obstructive CAD through the use of a deep learning model trained using polar maps, similar concepts can be applied to other fields to likewise enable improvements to other technological processes. In such cases, any collected sensor data (e.g., imaging data or data from other sensors, such as an electrocardiogram (ECG)) can be used to train the deep learning model as disclosed herein and can be used to identify a desired output score (e.g., a probability of a diagnosable feature). In such cases, the techniques disclosed herein can allow an attention map to be generated that indicates the amount of information weight attributed to different regions of the collected sensor data. This attention map can then be presented alongside the output score, thus improving clinical translation and explainability of deep-learning-based techniques, leading to improved patient care.

For example, to help diagnose hypertrophic cardiomyopathy, instead of using training data associated with MPI studies (e.g., polar maps), the training data can be associated with electrocardiography (ECG) studies (e.g., a 12-lead electrocardiography study). In such an example, the outputs can be a hypertrophic cardiomyopathy score indicative of a probability of hypertrophic cardiomyopathy. Thus, ECG data can be supplied to the trained deep learning model to generate such a score, along with an ECG attention map indicating the areas of the ECG leading to an increased likelihood of hypertrophic cardiomyopathy. Similarly, certain aspects of the present disclosure could be used to highlight myocardial features of functionality significant coronary stenosis on coronary computed tomography or myocardial scar on cardiovascular magnetic resonance imaging.

In some cases, certain aspects of the present disclosure may be usable to identify hemodynamically significant stenosis.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a system 100 for training a deep learning model 102 for detecting obstructive coronary artery disease, according to certain aspects of the present disclosure. Training of the deep learning model 102 can occur over time and can be updated over time.

The deep learning model 102 can be trained by providing training data 104. Training data 104 can include a first dataset 106 and a second dataset 108. The first dataset 106 can include input data across a number of MPI studies, optionally including input data across a number of different sites, all collected using a first type of camera 110. The second dataset 108 can include input data across a number of MPI studies, optionally including input data across a number of different sites, all collected using a second type of camera 112. The first type of camera 110 can be different than the second type of camera 112. The first type of camera 110 can be a scintillation, or Anger, camera. The second type of camera 112 can be a CZT-based camera.

Training the deep learning model 102 can occur using known techniques for training deep neural networks, such as convolutional neural networks. Input data from the training data 104 can be supplied to the deep learning model 102 as appropriate, such as supplying polar maps at an input layer and supplying supplemental information at a (final) fully connected layer.

The resultant deep learning model 102 can be thus trained using multi-camera data. In some cases, however, the deep learning model 102 can be trained using only single-camera data, in which case the training data 104 would include only one of the first dataset 106 and the second dataset 108, but not both.

FIG. 2 is a schematic diagram depicting a system 200 for using a deep learning model 202 for detecting obstructive coronary artery disease, according to certain aspects of the present disclosure. The deep learning model 202 can be any suitable deep learning model as disclosed herein, such as deep learning model 102 of FIG. 1. The system 200 can be implemented using any suitable hardware, such as a computer workstation often used for viewing and/or analyzing MPI studies.

Input data 214 can be provided to the deep learning model 202, which can output results 220 (e.g., output data). The input data 214 can include a set of polar maps 216 and patient information 218 (e.g., supplemental information) for a single patient from a single MPI study. In some cases, the input data 214 can be from a supine MPI study, without additional data from an upright MPI study, although that need not always be the case.

The set of polar maps 216 can include at least one polar map. In some cases, the set of polar maps 216 can include a perfusion polar map, a motion polar map, and a thickening polar map. The perfusion polar map provides local information about the relative perfusion of the left ventricle (e.g., 0-100%), the motion map provides information about the motion of the left ventricle between systolic and diastolic phase (e.g., in mm), and the thickening map provides an amount of thickening (e.g., in %) of the left ventricle between the systolic phase and the diastolic phase. In some cases, the set of polar maps 216 includes any combination of two of the perfusion polar map, the motion polar map, and the thickening polar map. The patient information 218 can include age information (e.g., an age of the patient), sex information (e.g., a biological sex of the patient), and cardiac volume information (e.g., at least two of an EDV, an ESV, and/or a SV of the patient). The cardiac volume information can be that of the left ventricle.

The input data 214 can be applied to the deep learning model 202 as discussed herein, such as by providing the set of polar maps 216 to an input layer of the deep learning model 202 and providing the patient information 218 to (final) fully connected layers of the deep learning model 202.

As a result of providing the input data 214 to the deep learning model 202, the deep learning model 202, results 220 can be generated. Results 220 can include an attention map 222, a CAD scoring map 224, and a set of probabilities for obstructive CAD 226 (e.g., a set of CAD probabilities). In some cases, other CAD scoring data can be provided, and used as disclosed herein with reference to the set of probabilities for obstructive CAD 226, instead of or in addition to the set of probabilities for obstructive CAD 226. The set of probabilities for obstructive CAD 226 can be per vessel probabilities of CAD and/or an overall (e.g., general or "global") probability of CAD 227 for the heart. For example, the set of probabilities for obstructive CAD 226 can include any combination of one or more of a general probability of CAD 227, a probability of CAD in a LAD territory 228, a probability of CAD in a LCx territory 230, and a probability of CAD in a RCA territory 232.

Components of the results 220 can be generated by the deep learning model 202 and/or can be generated using outputs from the deep learning model 202. For example, the deep learning model 202 can generate the attention map 222 and the set of probabilities for obstructive CAD 226. Thereafter, the system 200 can generate the CAD scoring map 224 using the attention map 222 and the set of probabilities for obstructive CAD 226. In some cases, however, the CAD scoring map 224 is generated by the deep learning model 202.

FIG. 3 is a schematic diagram of a deep learning model 302 for detecting obstructive coronary artery disease, according to certain aspects of the present disclosure. The deep learning model 302 can be any suitable deep learning model as disclosed herein, such as deep learning model 102 of FIG. 1. The deep learning model 302 can be a deep neural network, such as a convolutional neural network.

The deep learning model 302 can include an input layer 350, a set of convolutional layers 352, a pooling layer 358, and a set of fully connected layers 360. The layers depicted and described with reference to FIG. 3 are for illustrative purposes, and in some cases, the deep learning model 302 can include more or fewer layers, including layers with different specifications than depicted with reference to FIG. 3.

Input data 314 can be provided to the deep learning model 302 to generate results 320 (e.g., output data). In at least some cases, the input data 314 can include a set of polar maps 316 that are provided to the input layer 350. The set of polar maps 316 can include a perfusion polar map, a motion polar map, and a thickening polar map. The input layer 350 can be sized to accept the set of polar maps 316, such as having a size of 64×64×3 to accept three polar maps each of size 64×64. Other sizes can be used.

The signals from the input layer 350 can be passed to the convolutional layers 352, such as to a first convolutional layer 354. The resultant signals can pass through any suitable number of convolutional layers until reaching a final convolutional layer 356. In an example, the signals from the input layer 350 can pass to a first convolutional layer 354 having a size of 64×64×32, the resultant signals of which pass to a final convolutional layer 356 having a size of 64×64×64. The filters of the convolutional layers 352 can be established during training for the purposes of providing the desired results 320. Each layer of the convolutional layers 352 can have a size that includes a length and width that is the same as the input layer 350, but with a depth dependent on the number of filters used for each of the convolutional layers 352. In some cases, the maximum depth of the first convolutional layer 354 is 32 and the maximum depth of the final convolutional layer 356 is 64, although that need not always be the case.

In some cases, some or all layers of the convolutional layers 352 can include Leaky ReLU activations having a negative slope (e.g., a negative slope of at or approximately 0.2). In some cases, the convolutional layers 352 can be regularized using dropout (e.g., with a probability of at or approximately 0.2) and a L2 kernel regularizer (e.g., with a rate of at or approximately 0.01 with a normal distribution). The outputs after the final convolutional layer 356 can be extracted using ReLu activations to generate the CAD attention map.

The signals from the final convolutional layer 356 can be passed to a pooling layer 358. The pooling layer 358 can have a size that includes a length and width smaller than the length and width of the final convolutional layer 356, but a depth the same as the depth of the final convolutional layer 356. In some cases, the length and width of the pooling layer 358 are based on the length and width dimensions of the final convolutional layer 356 divided by the stride size (e.g., filter size) of the final convolutional layer 356. For example, the pooling layer 358 can have a size of 32×32×64. In some cases, the pooling layer 358 is a max pooling layer, in which case the maximum value within a particular region of the final convolutional layer 356 is used as the corresponding value in the pooling layer 358. In some cases, however, other pooling schemes can be used (e.g., average pooling).

The signals from the pooling layer 358 can be passed to the fully connected layers 360. The fully connected layers 360 can include a final fully connected layer 364 and optionally additional layers, such as a first fully connected layer 362. The fully connected layers 360 can include a number of hidden units (e.g., at or approximately 128 hidden units) with L2 regularization and dropout (e.g., of at or about 0.3 each).

In some cases, the patient information 318 can be provided to a layer of the fully connected layers 360, such the final fully connected layer 364. The patient information 318 can be provided as numerical information. The patient information 318 can be concatenated to the final fully connected layer 364. The final fully connected layer 364 can compile the data extracted from the previous layers and the patient information 318 into the desired outputs 320. In an example, the desired outputs 320 can include CAD scoring data in the form of a set of three per-vessel probabilities of obstructive CAD (e.g., for LAD, LCx, and RCA) and a per-patient general probability of obstructive CAD. In such an example, the final fully connected layer 364 can use sigmoid activations to output a 1×4 vector of scoring data containing the per-vessel and per-patient probabilities.

In some cases, the deep learning model 302 can be trained using cross-entropy loss and Adam optimization with an initial learning rate of 0.001 and a batch size of 128 to optimize a multi-class multi-label classification loss. Hyper-parameters (e.g., stopping criteria and learning rate) can be tuned using 5-fold internal cross-validation.

Figure 4:
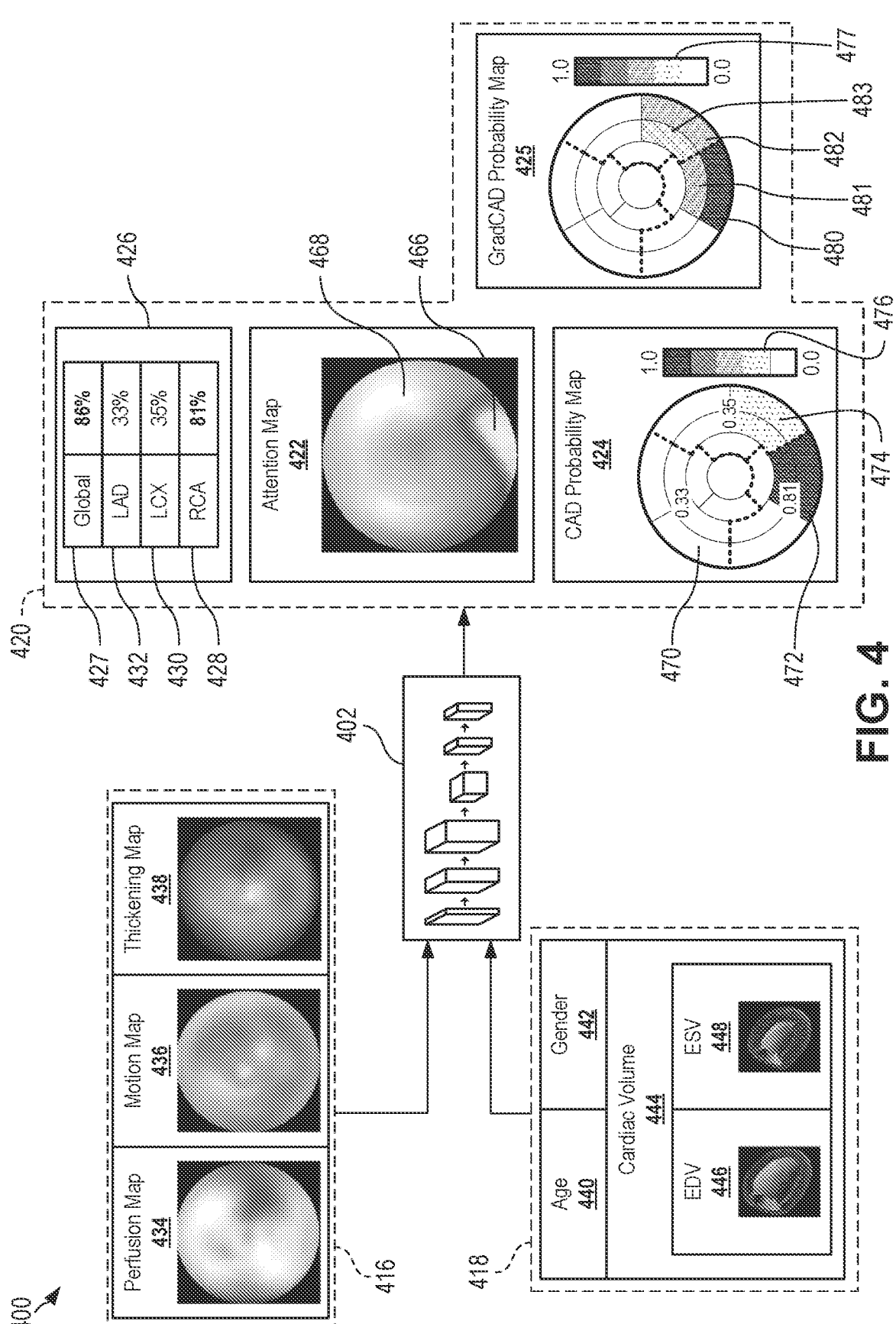
FIG. 4 is a schematic diagram depicting a system with example input data used to generate example results using a deep learning model for detecting obstructive coronary artery disease, according to certain aspects of the present disclosure.

FIG. 4 is a schematic diagram depicting a system 400 with example input data used to generate example results 420 using a deep learning model 402 for detecting obstructive coronary artery disease, according to certain aspects of the present disclosure. The deep learning model 402 can be any suitable deep learning model as disclosed herein, such as deep learning model 102 of FIG. 1.

The input data can include a set of polar maps 416 and patient information 418 associated with an MPI study. The set of polar maps 416 can include a perfusion map 434, a motion map 436, and a thickening map 438. These set of polar maps 416 can be from data acquired while the patient was in a supine position. The polar maps 416 can include raw gated and ungated polar maps. The polar maps 416 can be provided without the pre-defined coronary territories or assumed subdivisions.

The patient information 418 can include age information 440 (e.g., an age or age bracket of the patient), sex information 442 (e.g., a biological sex of the patient), and cardiac volume information 444. The cardiac volume information can include end-diastolic volume information 446 and end-systolic volume information 448.

The set of polar maps 416 and the patient information 418 can be provided to the deep learning model 402 to generate results 420. As described herein, the set of polar maps 416 can be provided to an input layer of the deep learning model 402 and the patient information 418 can be provided to a (final) fully connected layer of the deep learning model 402.

The deep learning model 402 can process the input data to produce results 420, which can include a set of probabilities of CAD 426, an attention map 422, and a CAD probability map 424 or other CAD scoring map. The set of probabilities of CAD 426 can include a global (e.g., per-patient or general) probability of CAD 427 and per vessel probabilities of CAD. Using the example input data of system 400, the set of probabilities of CAD 426 can include a global probability of CAD 427 of 80%, a probability of CAD in the LAD territory 428 of 33%; a probability of CAD in the LCx territory 430 of 35%; and a probability of CAD in the RCA territory 432 of 81%.

The attention map 422 generated by the deep learning model 402 can include an overlay 466 on a polar map 468. The polar map 468 can be one of the sets of polar maps 416 or a combination thereof. The overlay 466 can be an indication of regions of the polar map 468 that are important to the decision process of the deep learning model 402, at least with respect to the provided input data and generated results. The overlay 466 can be based on gradients of a predicted vessel flowing into the final convolutional layer of the deep learning model 402.

The CAD probability map 424 can be generated by the deep learning model 402 or generated from outputs of the deep learning model 402. The CAD probability map 424 can include a segmented map of a heart that is coded (e.g., color-coded) based on probability of CAD and the segments which are highlighted in the CAD attention map. If the segments are not highlighted in the CAD attention map, the corresponding segments on the CAD probability map 424 can remain color-coded as low (e.g., at or near 0.0 on scale 476). In some cases, the CAD probabilities from the set of probabilities of CAD 426 can be overlaid on the CAD Probability Map 424 in regions corresponding to the associated territories of the heart. For example, the CAD probability map 424 can include a first region 470 that includes segments associated with the CAD probability in the LAD territory (e.g., 33%); a second region 472 that includes segments associated with the CAD probability in the RCA territory (e.g., 81%); and a third region 474 that includes segments associated with the CAD probability in the LCx territory (e.g., 35%). In some cases, an indication of the global probability of CAD 427 (e.g., 88%) can be optionally presented in conjunction with (e.g., adjacent to) the CAD Probability Map 424.

Each of the segments of each territory can be coded based on a scale 476. In some cases, segments not contributing to the deep learning prediction (e.g., not highlighted by overlay 466 for which the determined level of interest is below a threshold) are not coded or are coded at or near 0.0. As depicted in FIG. 4, an illustrative version of scale 476 can include five categories, each having a unique pattern. The lowest category on the scale 476 can represent CAD probability in the range of 0.0 (0%) up to 0.2 (20%); the next category can represent CAD probability in the range of 0.2 (20%) up to 0.4 (40%); the next category can represent CAD probability in the range of 0.4 (40%) up to 0.6 (60%); the next category can represent CAD probability in the range of 0.6 (60%) up to 0.8 (80%); and the top category on the scale 476 can represent CAD probability in the range of 0.8 (80%) up to 1.0 (100%). While patterns are used to designate categories in the scale 476 depicted in FIG. 4, other discernable features can be used, such as colors, highlighting, flashing, or any other suitable discernable indicator.

For the CAD Probability Map 424 depicted in FIG. 4, it will be noted that despite the second region 472 being associated with the LAD territory, which has a CAD percentage of 33%, not all segments within the second region 472 are coded for the 33% probability. Rather, only segments that are sufficiently of interest, as depicted in the Attention Map 422, are coded according to the 33% probability. Therefore, all segments within the second region 472 are left uncoded or are coded using the lowest category except for the outermost and second-outermost segments of the CAD Probability Map 424 nearest the bottom of FIG. 4 (e.g., the outermost and second-outermost segments at the 6 o'clock position). Likewise, all segments of the first region 470 and the three segments nearest the top of FIG. 4 from the third region 474 are left uncoded or are coded using the lowest category. The two segments nearest the bottom of FIG. 4 from the third region 474 are coded according to the 35% CAD probability for the LCx territory, which is associated with the third region 474.

In some cases, results 420 can include a gradCAD Probability Map 425. The gradCAD Probability Map 425 can be generated by the deep learning model 402 or generated from outputs of the deep learning model 402. The gradCAD probability map 425 can include a segmented map of a heart that is coded (e.g., color-coded) based on the indication of regions of at least one of the set of polar maps 416 that are important to the decision process of the deep learning model 402, at least with respect to the provided input data and generated results. In some cases, the gradCAD probability map 425 can be made using the overlay 466 from the attention map 422. The coding of each segment of the gradCAD probability map 425 can be based on the amount (and optionally strength) of highlighted portions of the attention map 422 that exist within that particular segment. Thus, for regions where the attention map 422 is not highlighted (e.g., where there is no indication that the region is important or where the indication that the region is important is below a threshold amount), the corresponding segment in the gradCAD probability map 425 would remain uncoded or coded as low or none. However, regions where the attention map 422 shows importance, such as the highlighted region of overlay 466, will cause the corresponding segment in the gradCAD Probability Map 425 to be coded as higher than non or otherwise coded depending on the amount (and optionally intensity) of highlighting that falls within that segment.

For example, a scale 477 can include a coding gradient (e.g., a color gradient) that extends from 0.0 (0%) to 1.0 (100%). This scale 477 can be segmented, like scale 476, or can be continuous (as shown). In some cases, each segment of the gradCAD Probability Map 425 is coded based on the amount of the segment covered by the highlighting from overlay 466 of the attention map 422.

In the example depicted in FIG. 4, the highlighting from overlay 466 of the attention map 422 covers most of segment 480, a moderate amount of segment 481 and segment 482, and a small amount of segment 484. For example, the amount the highlighted region from overlay 466 covers these segments may be approximately 80% for segment 480, approximately 40% for segment 481, approximately 35% for segment 482, and approximately 20% for segment 483. Thus, segments 480, 481, 482, 483 are coded appropriately, according to scale 477. Because the highlighting from overlay 466 of the attention map 422 does not cover any of the remaining segments, they are left uncoded or coded as the lowest amount (e.g., 0% or 0.0).

Figure 5:
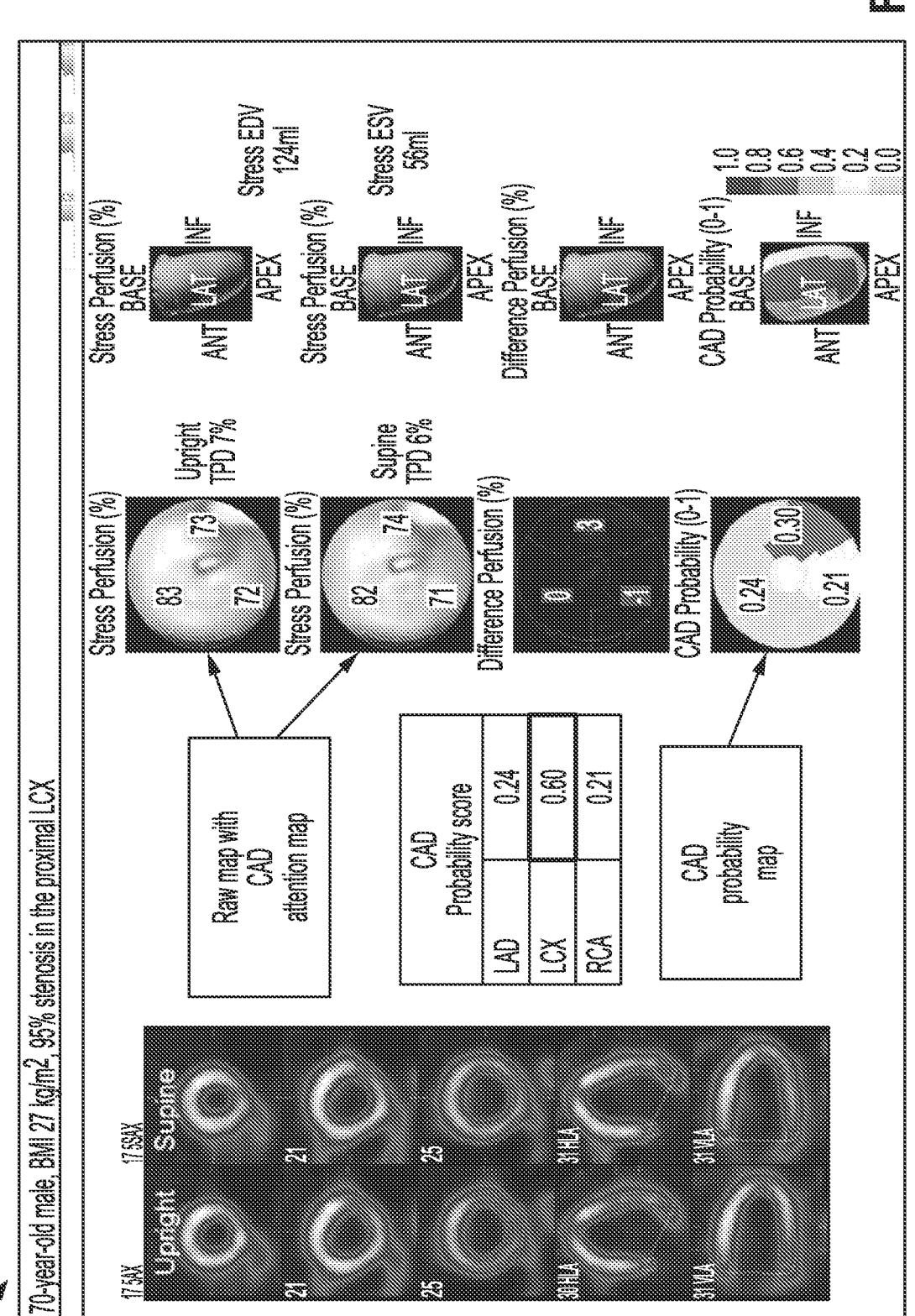
FIG. 5 is a set of diagrams depicting myocardial perfusion imaging study input data and results from applying the input data to a deep learning model for detecting obstructive coronary artery disease, according to certain aspects of the present disclosure.

FIG. 5 is a set of diagrams 500 depicting results from applying myocardial perfusion imaging study input data to a deep learning model for detecting obstructive coronary artery disease, according to certain aspects of the present disclosure.

The set of diagrams 500 are associated with a MPI study on an example 70 year old male patient with a body mass index (BMI) of 27 kg/m$^2$ who had a 95% stenosis in the proximal LCx. The patient had a stress EDV of 124 ml and a stress ESV of 56 ml. In this case, the stress TPD as separately calculated was 7% at upright, 6% at supine, and 4% for combined, whereas visual assessment was interpreted as normal. The CAD probability map (center bottom) showed high probability of CAD in the LCx territory and also highlighted the segments with activation in the 17-segment model in the LCx territory.

At the far left of the set of diagrams 500 are depicted a series of upright and supine images showing stress SPECT MPI (left) and stress gated SPECT (right).

Near the top center of the of diagrams 500 are depicted an upright attention map and a supine attention map. The upright attention map was generated using a set of polar maps taken during upright scans in the MPI study, whereas the supine attention map was generated using a set of polar maps taken during supine scans in the MPI study. A TPD of 7% was separately calculated for the upright scans and a TPD of 6% was separately calculated for the supine scans. Each of the attention maps is depicted as an overlay on a raw polar map. Below the two polar maps is a segmented diagram depicting the percentage difference in perfusion.

When the myocardial perfusion imaging study input data from larger populations of data (e.g., the data referenced with respect to FIG. 9) is applied to the trained deep learning model as disclosed herein, it has been determined that the attention map generally highlights at least 44% of mild perfusion deficits and at or approximately 100% of moderate perfusion deficits. It was also determined that the area of attention in the polar maps correlates (with p<0.001) with the areas that have quantitative perfusion deficits in the polar maps for the whole coronary, LAD, LCx, and RCA territories.

Left of the center of the set of diagrams 500 is a chart depicting CAD probability scores for the LAD, LCx, and RCA territories. These probabilities are 0.24, 0.60, and 0.21 for LAD, LCx, and RCA, respectively. While not depicted, in some cases the CAD probability scores can include a global probability of CAD score.

Near the bottom center of the diagrams 500 is a CAD probability map. The CAD probability map depicts color-coded segments based on the CAD probability scores and the attention map(s).

On the right side of the set of diagrams 500, from top to bottom, are depicted a three-dimensional representations of a heart showing: i) the percentage of stress perfusion for upright scans; ii) the percentage of stress perfusion for supine scans; iii) the percentage difference of perfusion; and iv) a segmented CAD probability map.

As depicted in the set of diagrams 500, determination of and explanation of the patient's obstructive CAD can be facilitated using the CAD probability scores, the attention maps, and the CAD probability maps.

Figure 6:
FIG. 6 is a schematic diagram depicting a 10-fold testing scheme for testing and training a deep learning model for detecting obstructive coronary artery disease, according to certain aspects of the present disclosure.

FIG. 6 is a schematic diagram 600 depicting a 10-fold testing scheme for training and testing a deep learning model for detecting obstructive coronary artery disease, according to certain aspects of the present disclosure. The testing scheme of FIG. 6 can be used to test any suitable deep learning model as disclosed herein, such as deep learning model 100 of FIG. 1.

In the example depicted in diagram 600, 3578 patients (62.8%, 2247 of which had obstructive CAD) were tested using 10-fold repeated testing and external testing. For repeated testing, the dataset was randomly split into 10 folds resulting in 90-10 stratified split, thus equal percentage of samples with CAD were maintained. Each fold with 90% of the total data was further 75-25 stratified split into 5 validation folds for model hyperparameter optimization, such as learning rate, stopping criteria, and the like. The final hold-out with 10% of the data was then tested with the hyperparameters selected. The repeated testing predictions were subsequently merged, thus evaluating the entire dataset.

Figure 7:
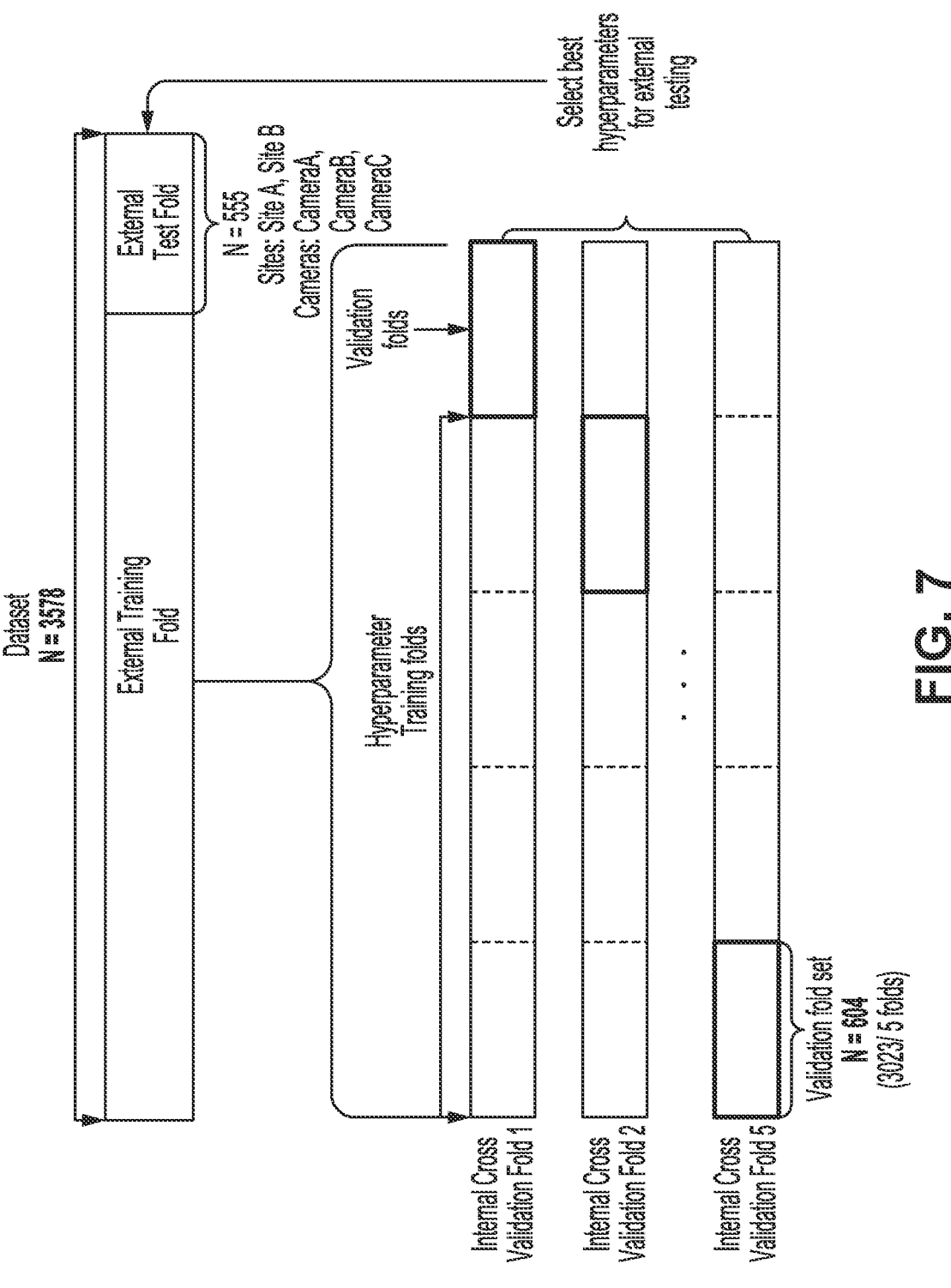
FIG. 7 is a schematic diagram depicting an external testing scheme for testing and training a deep learning model for detecting obstructive coronary artery disease, according to certain aspects of the present disclosure.

FIG. 7 is a schematic diagram 700 depicting an external testing scheme for testing and training a deep learning model for detecting obstructive coronary artery disease, according to certain aspects of the present disclosure. The testing scheme of FIG. 7 can be used to test any suitable deep learning model as disclosed herein, such as deep learning model 100 of FIG. 1. As described with reference to diagram 7000, the same dataset from FIG. 6 can be used.

The model was internally 5-fold cross validated using 3023 patients for hyperparameter optimization as indicated with respect to FIG. 6. Therefore, the generalizability of the deep learning model prediction to new MPI data was determined by evaluating unseen patients from the held-out set containing each camera type. External testing assesses the accuracy of a model in patients from a different, but plausibly related, population.

The expected performance of the deep learning model can be externally tested on unseen data by holding out patients from sites Site A and Site B, which were scanned using CameraA, CameraB, and CameraC cameras resulting in an external hold-out test set of 555 patients (59%, 329 of which had obstructive CAD). Cameras CameraA, CameraB, and CameraC included at least one camera of the Anger type and at least one camera of the CZT type.

Figure 8:
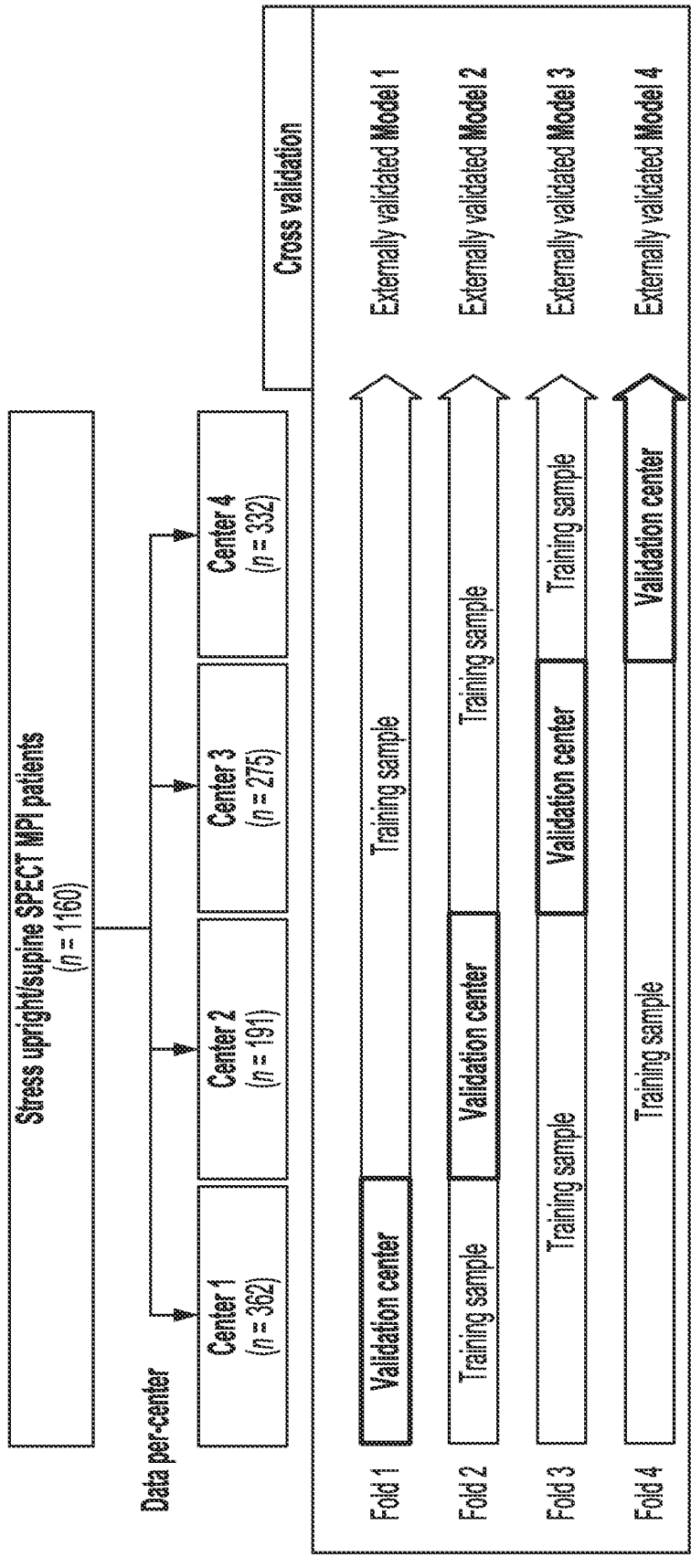
FIG. 8 is a schematic diagram depicting a leave-one site out testing scheme for testing and training a deep learning model for detecting obstructive coronary artery disease, according to certain aspects of the present disclosure.

FIG. 8 is a schematic diagram depicting a leave-one site out testing scheme for testing and training a deep learning model for detecting obstructive coronary artery disease, according to certain aspects of the present disclosure. The testing scheme of FIG. 8 can be used to test any suitable deep learning model as disclosed herein, such as deep learning model 100 of FIG. 1. The testing scheme of FIG. 8 can be especially useful for testing deep learning models trained on single-camera, multi-site datasets. In some cases, the testing scheme of FIG. 8 can additionally include elements of testing schemes of FIGS. 6-7.

Because a single-camera, multi-site dataset generally has a balanced population in each site, the deep learning model can be tested by leaving one site out for each of the site folds. This approach can validate the model on unseen site data for each fold assessing the model performance from a same camera type.

Figure 9:
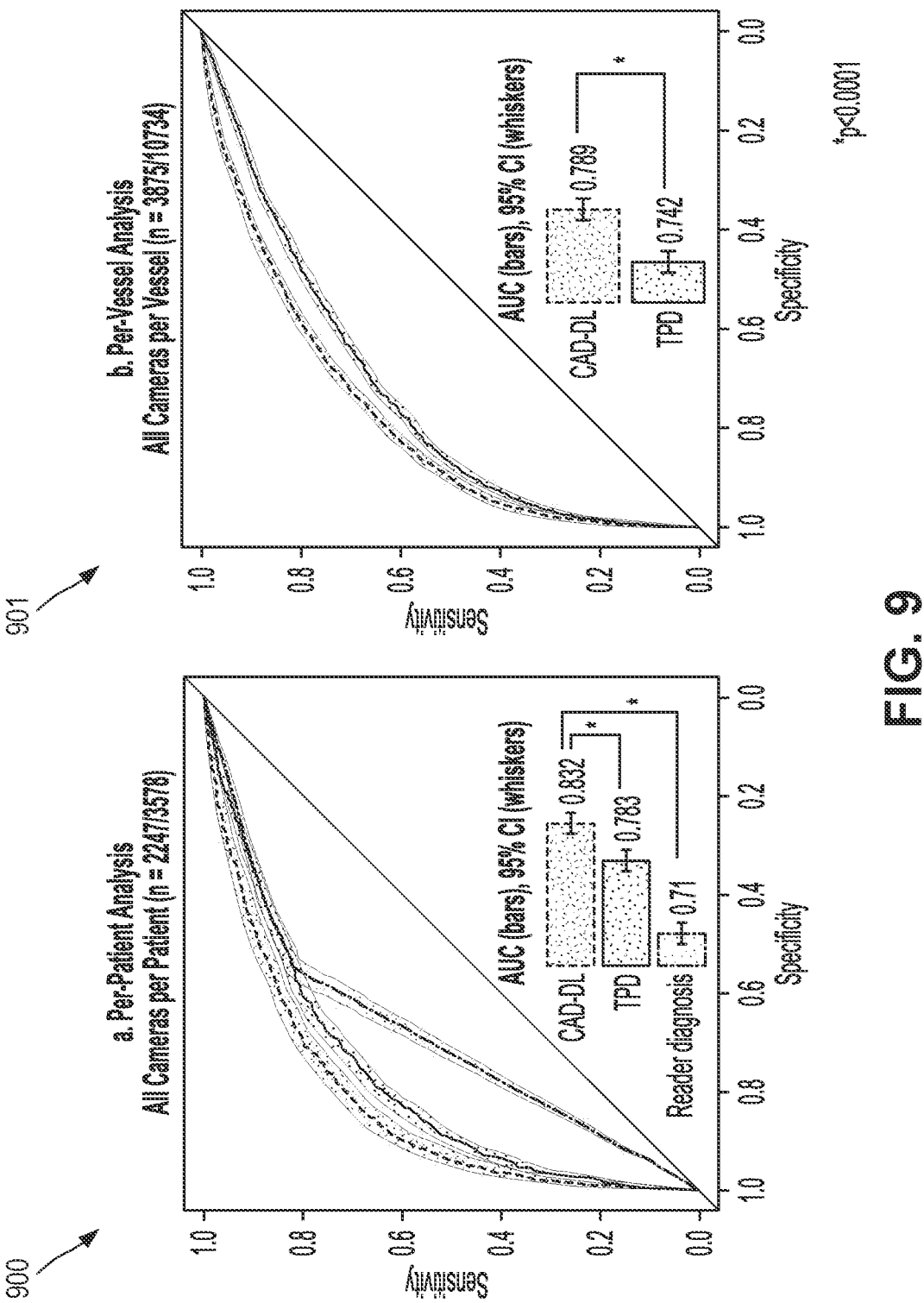
FIG. 9 is a set of sensitivity-specificity charts depicting per-patient analysis results and per-vessel analysis results for a deep learning model for detecting obstructive coronary artery disease as tested using a 10-fold testing scheme, according to certain aspects of the present disclosure.

FIG. 9 is a set of sensitivity-specificity charts 900, 901 depicting per-patient analysis results and per-vessel analysis results for a deep learning model for detecting obstructive coronary artery disease as tested using a 10-fold testing scheme, according to certain aspects of the present disclosure. The 10-fold testing scheme can be the same testing scheme as described with reference to FIG. 6.

The sensitivity and specificity curves are depicted for the deep learning model ("CAD-DL") and for a Stress Total Perfusion Deficit analysis approach ("TPD"). The diagnostic thresholds were set as 4.3% for stress TPD and 0.45 for per-patient CAD-DL to match the specificity of "abnormal" reader diagnosis. The area under the sensitivity-specificity curve (AUC) is depicted in bar graph form, with whiskers showing a 95% confidence interval. The greater the AUC, the better the diagnosis methodology (e.g., greater numbers of true positive determinations of the presence of CAD and true negative determinations of the lack of CAD). Chart 900 depicts a per-patient analysis for the prediction of obstructive CAD. Chart 900 additionally depicts the curve and AUC for a visual perfusion assessment ("reader diagnosis"). The deep learning model provided a significantly higher AUC compared to visual perfusion assessment and stress TPD analysis. The results are significant because the of a p value below 0.0001 for all.

Chart 901 depicts a per-vessel analysis for the prediction of obstructive CAD. The deep learning model provided a significantly higher AUC compared to stress TPD analysis. The results are significant because the of a p value below 0.0001. The sensitivity was higher by CAD-DL compared to stress TPD or reader diagnosis.

While not depicted, a subset of the data referenced with respect to charts 900, 901 that is associated with a population of individuals with a low-likelihood of obstructive CAD was reviewed. It was determined that the normalcy rate by CAD-DL (88%) was higher than TPD (82%) or visual diagnosis (79%) (p<0.0001 for both). In a population undergoing SPECT and CCTA, the prevalence of obstructive CAD observed in CCTA was 12%. The per-patient AUC [95% CI] for CAD-DL was 0.75 [0.65-0.85] and for TPD 0.67 [0.56-0.78], (p=0.14). The per-vessel AUC [95% CI] of CAD-DL (0.75 [0.67-0.83]) was higher compared to stress TPD (0.64 [0.55-0.74], p=0.01).

Figure 10:
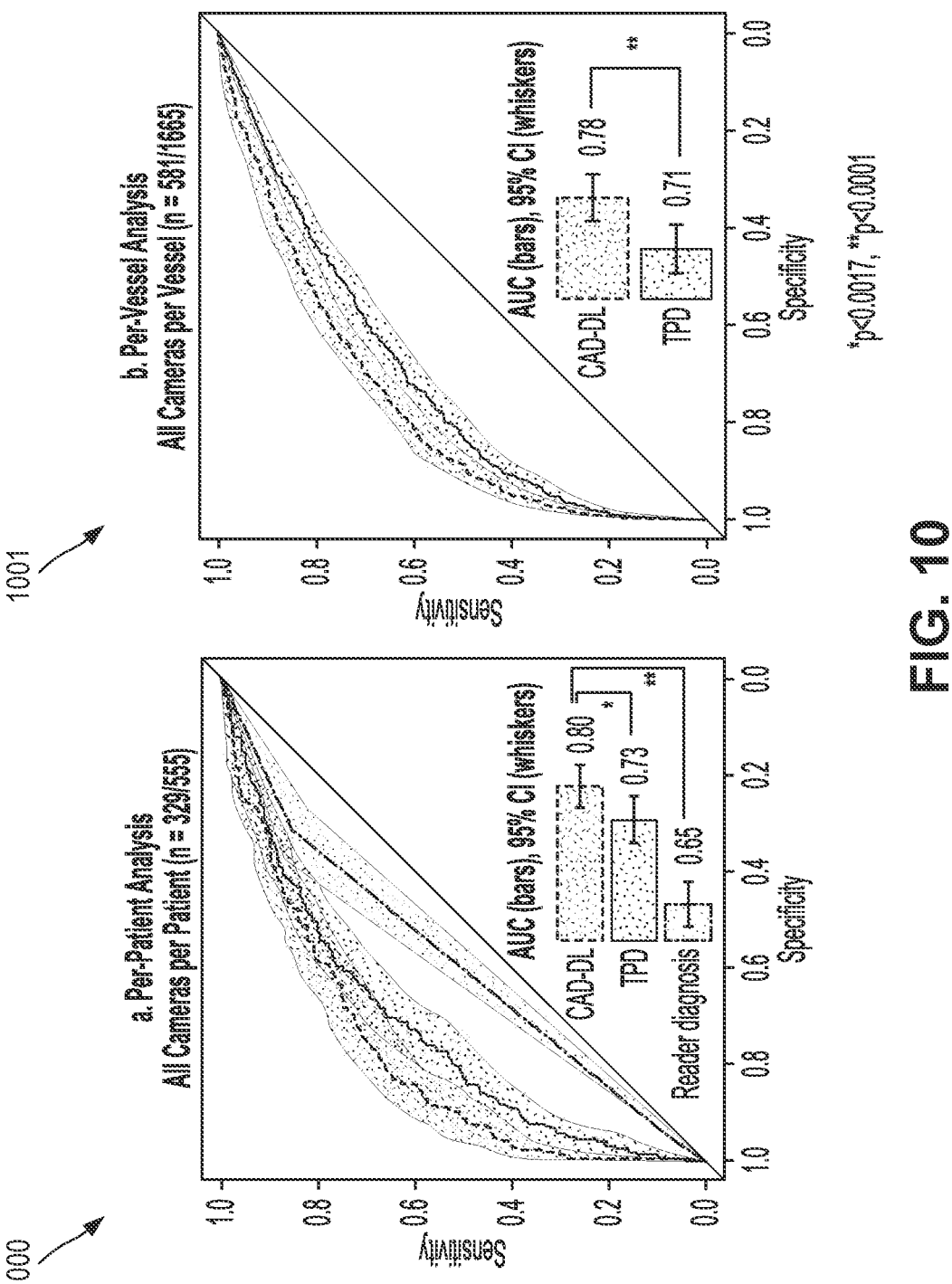
FIG. 10 is a set of sensitivity-specificity charts depicting per-patient analysis results and per-vessel analysis results for a deep learning model for detecting obstructive coronary artery disease as tested using an external testing scheme, according to certain aspects of the present disclosure.

FIG. 10 is a set of sensitivity-specificity charts depicting per-patient analysis results and per-vessel analysis results for a deep learning model for detecting obstructive coronary artery disease as tested using an external testing scheme, according to certain aspects of the present disclosure. The external testing scheme can be the same testing scheme as described with reference to FIG. 7.

The sensitivity and specificity curves are depicted for the deep learning model ("CAD-DL") and for a Stress Total Perfusion Deficit analysis approach ("TPD"). The area under the sensitivity-specificity curve (AUC) is depicted in bar graph form, with whiskers showing a 95% confidence interval. The greater the AUC, the better the diagnosis methodology (e.g., greater numbers of true positive determinations of the presence of CAD and true negative determinations of the lack of CAD).

Chart 1000 depicts a per-patient analysis for the prediction of obstructive CAD. Chart 1000 additionally depicts the curve and AUC for a visual perfusion assessment ("reader diagnosis"). The deep learning model provided a significantly higher AUC compared to visual perfusion assessment and stress TPD analysis. The results are significant because the of a p value below 0.01 for TPD and 0.0001 for reader diagnosis.

Chart 1001 depicts a per-vessel analysis for the prediction of obstructive CAD. The deep learning model provided a significantly higher AUC compared to stress TPD analysis. The results are significant because the of a p value below 0.0001.

Figure 11:
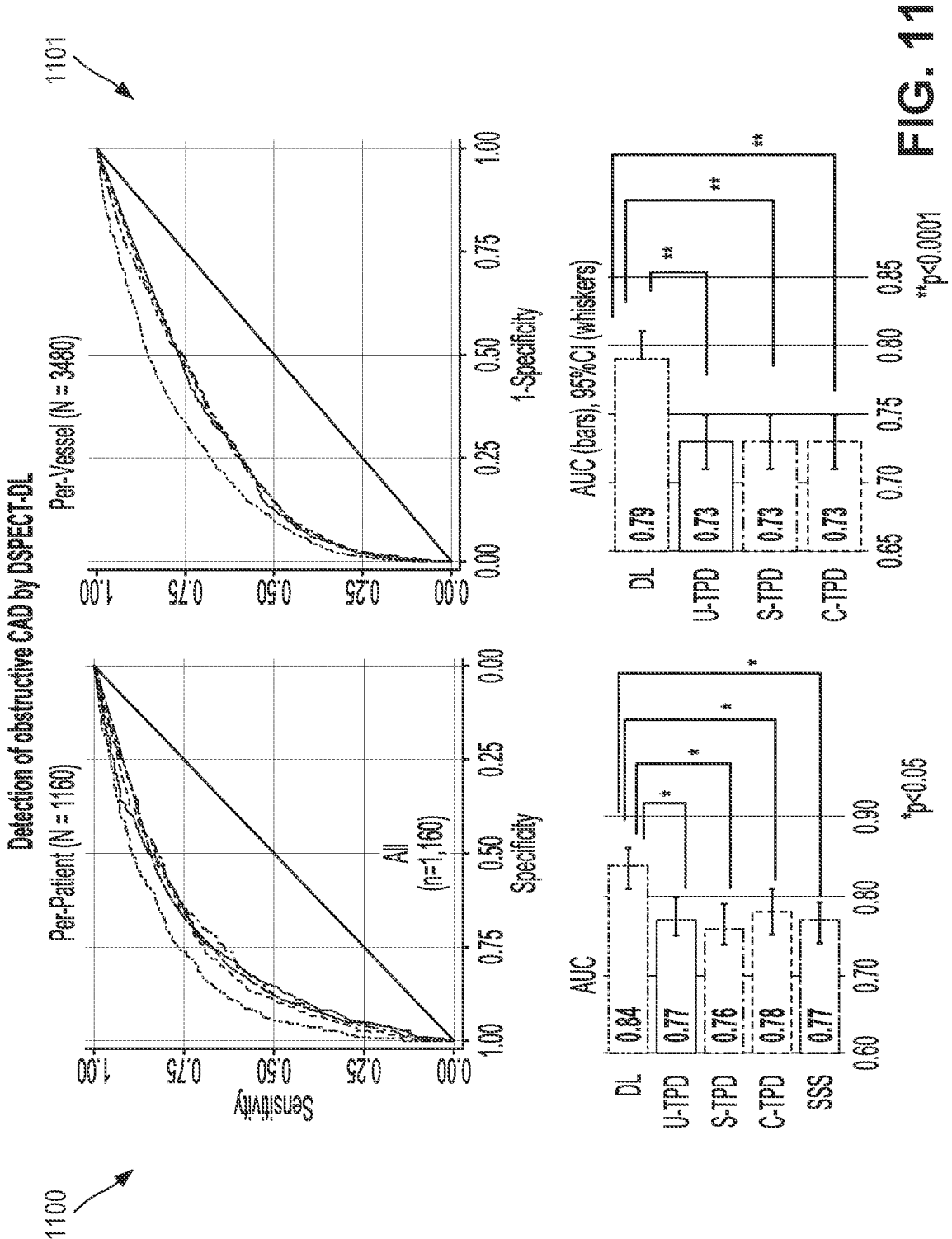
FIG. 11 is a set of sensitivity-specificity charts depicting per-patient analysis results and per-vessel analysis results for a deep learning model for detecting obstructive coronary artery disease as tested using a leave-one site out testing scheme, according to certain aspects of the present disclosure.

FIG. 11 is a set of sensitivity-specificity charts depicting per-patient analysis results and per-vessel analysis results for a deep learning model for detecting obstructive coronary artery disease as tested using a leave-one site out testing scheme, according to certain aspects of the present disclosure. The leave-one site out testing scheme can be the same testing scheme as described with reference to FIG. 8.

The sensitivity and specificity curves are depicted for the deep learning model ("DL"), an upright Total Perfusion Deficit analysis approach ("U-TPD"), a supine TPD analysis approach ("S-TPD"), and a combined upright and supine TPD analysis approach ("C-TPD"). The area under the sensitivity-specificity curve (AUC) is depicted in bar graph form, with whiskers showing a 95% confidence interval. The greater the AUC, the better the diagnosis methodology (e.g., greater numbers of true positive determinations of the presence of CAD and true negative determinations of the lack of CAD).

Chart 1100 depicts a per-patient analysis for the prediction of obstructive CAD. Chart 1100 additionally depicts the curve and AUC for a summed stress score analysis approach ("SSS"). For all TPD measurements on both acquisitions and the deep learning model, the diagnostic cutoff values were established to show the same specificities as SSS≥4. The deep learning model provided a significantly higher AUC compared to SSS (p<0.05), U-TPD (p<0.05) or S-TPD (p<0.05), or C-TPD (<0.05). The results are significant because the p values provided.

Chart 1101 depicts a per-vessel analysis for the prediction of obstructive CAD. The deep learning model provided a significantly higher AUC compared to U-TPD, S-TPD, and C-TPD. The results are significant because the of a p value below 0.0001.

Figure 12:
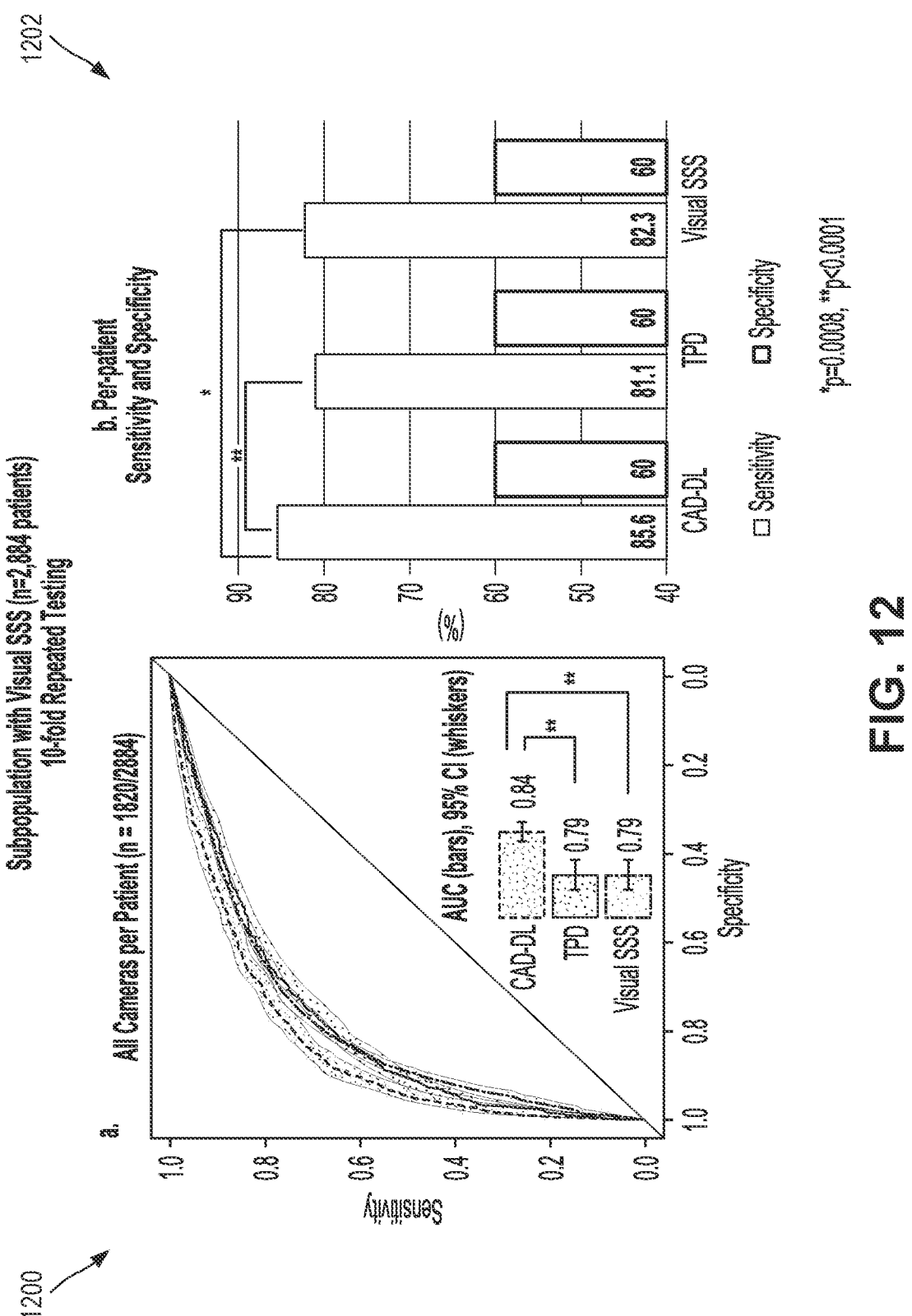
FIG. 12 is a set of sensitivity-specificity charts depicting per-patient analysis results for a deep learning model for detecting obstructive coronary artery disease as compared to total perfusion deficit and visual segmented scoring, according to certain aspects of the present disclosure.

FIG. 12 is a set of sensitivity-specificity charts 1200, 1202 depicting per-patient analysis results for a deep learning model for detecting obstructive coronary artery disease as compared to total perfusion deficit and visual segmented scoring, according to certain aspects of the present disclosure.

Of the patient data referenced with respect to FIG. 9, visual summed stress scores (SSS) were available for a subpopulation of 2,884 patients. It was determined that the per-patient AUC by CAD-DL was higher compared to the SSS or stress TPD while there was no substantial difference between SSS and stress TPD. The sensitivity and specificity of SSS≥4 was 82.3% and 60%, respectively. The sensitivity was higher by CAD-DL (85.6%) compared to stress TPD or SSS. There was no substantial difference in sensitivity between stress TPD and SSS (p=0.18).

Figure 13:
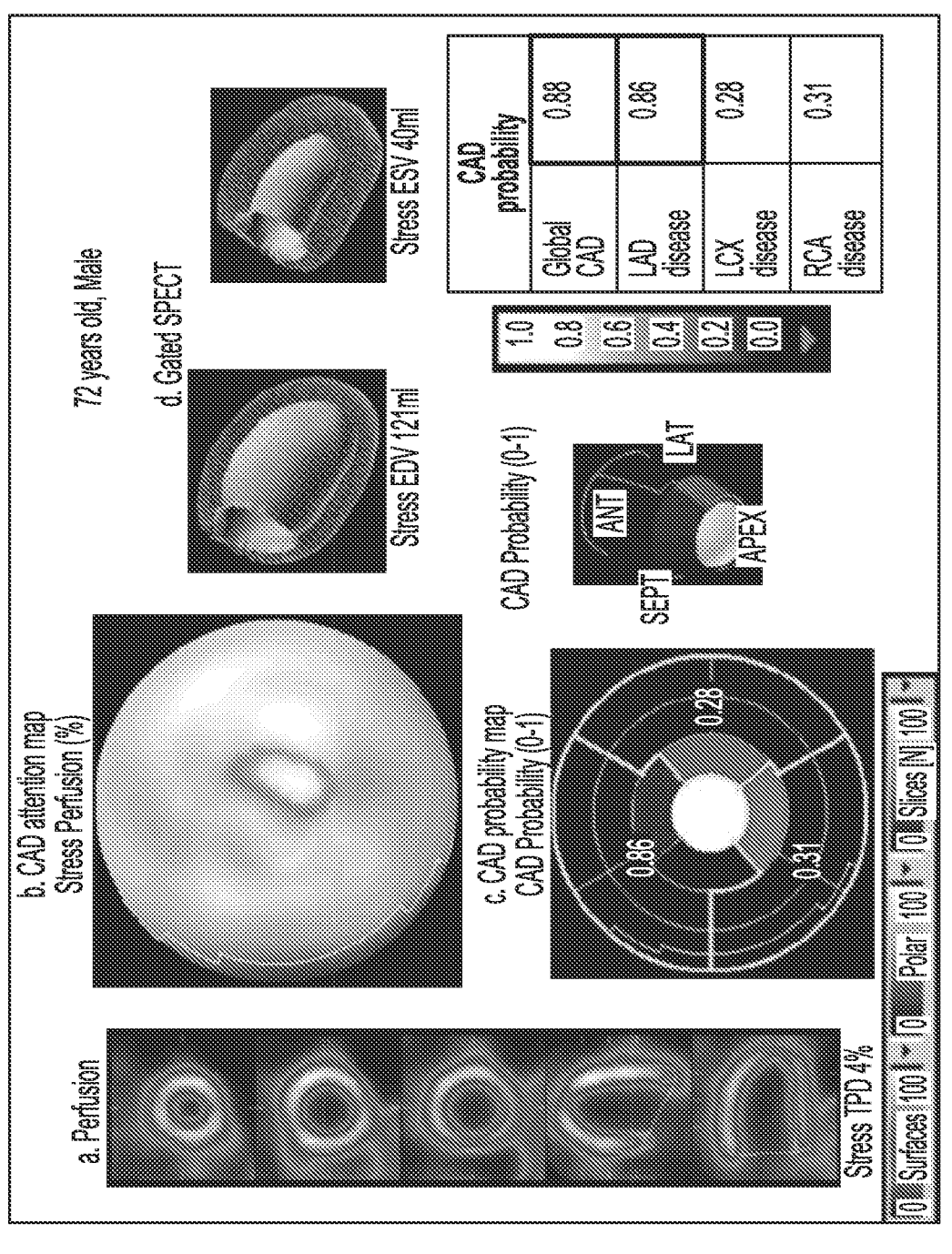
FIG. 13 is a set of diagrams depicting myocardial perfusion imaging study input data and results from applying the input data to a deep learning model for detecting obstructive coronary artery disease, according to certain aspects of the present disclosure.

FIG. 13 is a set of diagrams 1300 depicting myocardial perfusion imaging study input data and results from applying the input data to a deep learning model for detecting obstructive coronary artery disease, according to certain aspects of the present disclosure.

The set of diagrams 1300 are associated with a MPI study on an example 72 year old male patient with an 85% stenosis in the proximal LAD artery on coronary angiography. The stress images (a) were assessed visually and interpreted as equivocal (SSS=2). The CAD attention map (b) highlights image regions contributing to the CAD prediction overlaid onto a perfusion polar map. The CAD probability map (c) shows a high probability of CAD and specifically LAD disease with the distal anterior and apical segments contributing to the prediction. The left ventricular volumes (d) are depicted and calculated from gated SPECT. Finally, the various CAD probabilities are depicted, including a global CAD probability of 0.88, a LAD disease probability of 0.86, an LCx disease probability of 0.28, and an RCA disease probability of 0.31. As depicted in diagrams 1300, CAD probability maps can be present in a two dimensional and/or three dimensional map.

As depicted in the set of diagrams 1300, determination of and explanation of the patient's obstructive CAD can be facilitated using the CAD probability scores, the attention maps, and the CAD probability maps.

Figure 14:
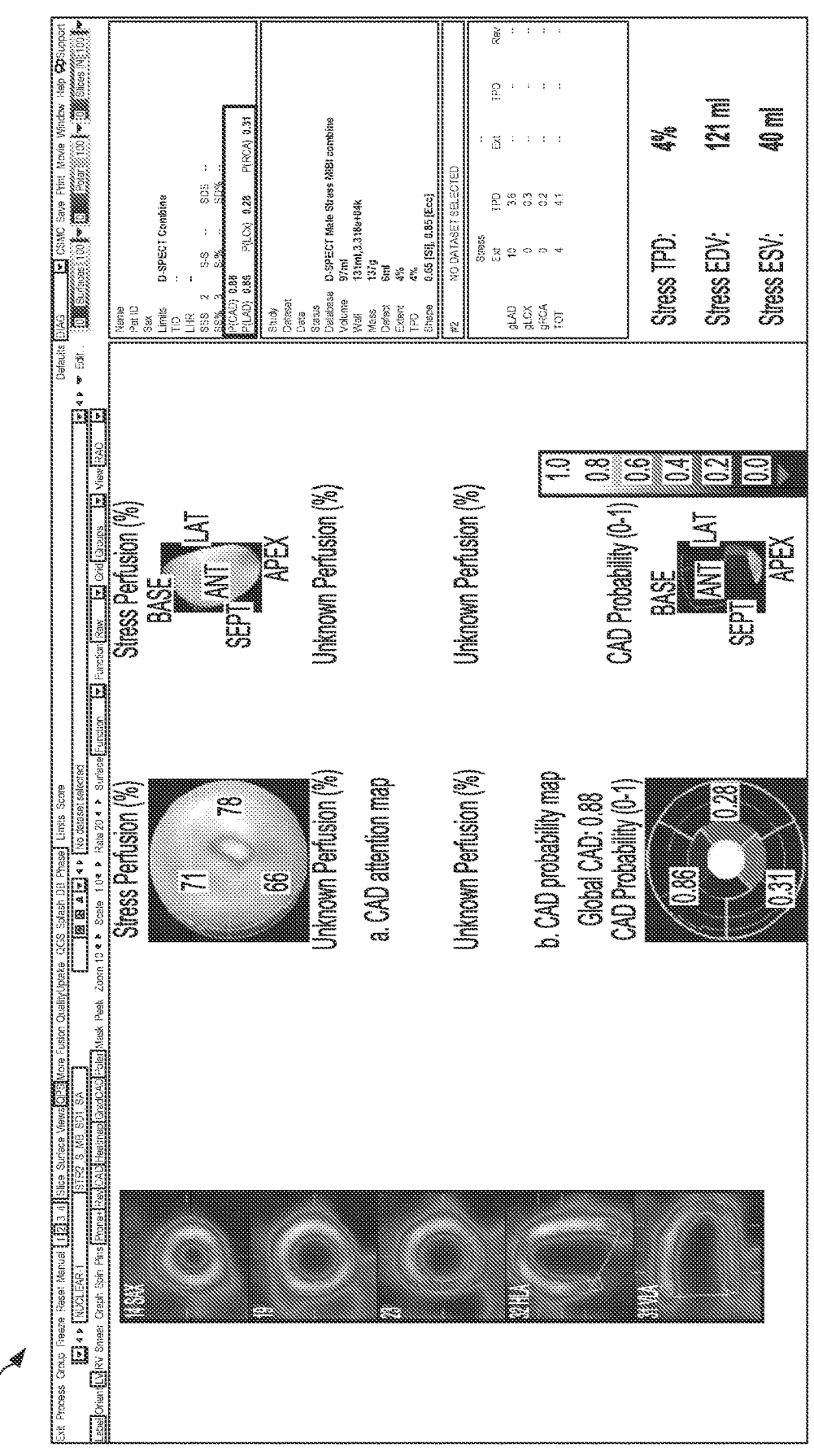
FIG. 14 is an example graphical user interface for evaluating myocardial perfusion imaging study input data for obstructive coronary artery disease, according to certain aspects of the present disclosure.

FIG. 14 is an example graphical user interface 1400 for evaluating myocardial perfusion imaging study input data for obstructive coronary artery disease, according to certain aspects of the present disclosure. The graphical user interface (GUI) 1400 can depict the set of diagrams 1300 of FIG. 13, as well as additional data.

Additional data presented alongside the set of diagrams 1300 can include information about the imaging study (e.g., type of equipment used, position of the patient, etc.), CAD scoring data (e.g., probabilities of obstructive CAD globally and per territory), information about the deep learning model being used, patient information, SSS information, TPD information, stress EDV and stress ESV, and other such information.

In some cases, the GUI 1400 can include buttons to add or remove individual aspects of the set of diagrams 1300. For example, buttons can be used to toggle the display of polar maps, CAD attention maps, CAD probability maps, CAD scoring data, and the like. Additionally, buttons can be used to change the presentation of information between different formats, such as between a 2-dimensional CAD probability map and a 3-dimensional CAD probability map.

In some cases, the GUI 1400 can include input functionality to allow a user to input additional information associated with the patient. The additional information can be used to dynamically update the set of diagrams 1300 and/or other information displayed on the GUI 1400. For example, a user may input an update to the user's age information, which may cause the deep learning model to output a slightly different global CAD probability, which will be dynamically updated on the GUI 1400.

FIG. 15 is a flowchart depicting a process 1500 for using a deep learning model for detecting obstructive coronary artery disease, according to certain aspects of the present disclosure. The process 1500 can be used with any suitable deep learning model as disclosed herein, such as deep learning model 100 of FIG. 1.

At block 1502, input data is received. The input data is associated with a myocardial perfusion imaging study. A myocardial perfusion imaging study can include one or more scans of a patient's heart to detect a radioactive tracer. The input data can include a set of polar maps and patient information. The set of polar maps can include a perfusion map, a motion map, and a thickening map. The patient information can include age information, sex information, and cardiac volume information.

At block 1504, the input data is provided to a deep learning model. Providing the input data at block 1504 can include providing the set of polar maps at an input layer of the deep learning model. Providing the input data at block 1504 can include providing the patient information at a (final) fully connected layer of the deep learning model. In some cases, providing input data at block 1504 does not include providing information about the type of camera used to generate the set of polar maps.

At block 1506, CAD scoring data (e.g., a set of probabilities for obstructive CAD) can be generated. Generating the CAD scoring data can include passing the input data through the deep learning model. Generating CAD scoring data can be in response to providing the input data to the deep learning model at block 1504. Generating the CAD scoring data at block 1506 can include generating a probability of CAD for each of a set of vessels or vessel territories of the heart and/or generating a general probability of CAD for the heart. The set of vessels or vessel territories can include one for general probability, one for LAD, one for LCx, one for RCA, or any combination thereof.

At block 1508, an attention map can be generated. Generating the attention map can include passing the input data through the deep learning model. Generating the attention map can be in response to providing the input data to the deep learning model at block 1504. Generating the attention map can include generating an overlay indicative of regions of importance associated with the CAD scoring data. The regions of importance can be those regions of one or more of the polar maps from block 1502 that were of importance to generating the set of probabilities at block 1506. These regions of importance can be determined by applying gradients of a predicted vessel to a final convolution layer to produce a coarse localization map. The coarse localization map can be applied to one or more of the polar maps from block 1502 to generate the attention map.

At block 1510, a CAD scoring map (eg., a CAD probability map) can be generated. Generating the CAD scoring map can include passing the input data through the deep learning model. Generating the CAD scoring map can be in response to providing the input data to the deep learning model at block 1504. Generating the CAD scoring map can be in response to generating the CAD scoring data (e.g., set of probabilities) at block 1506 and generating the attention map at block 1508. Generating the CAD scoring map can include segmenting the attention map and flagging segments of the segmented attention map based on the CAD scoring data generated at block 1506. Generating the CAD scoring map can include determining severity measurements for each segment. Generating the CAD scoring map can include presenting a differentiable visual indicator on each of the segments based on the determined severity measurement. In some cases, the differentiable visual indicator is a category-based color code.

At block 1512, the results from the deep leaning model can be presented. Results can be presented on a display device. Presenting the results at block 1512 can include presenting the CAS scoring data at block 1514; presenting the attention map at block 1516; and presenting the CAD scoring map at block 1518. As used herein, presenting CAD scoring data at block 1514 can include presenting some or all of the CAD scoring data itself or presenting information obtained from some or all of the CAD scoring data.

Figure 16:
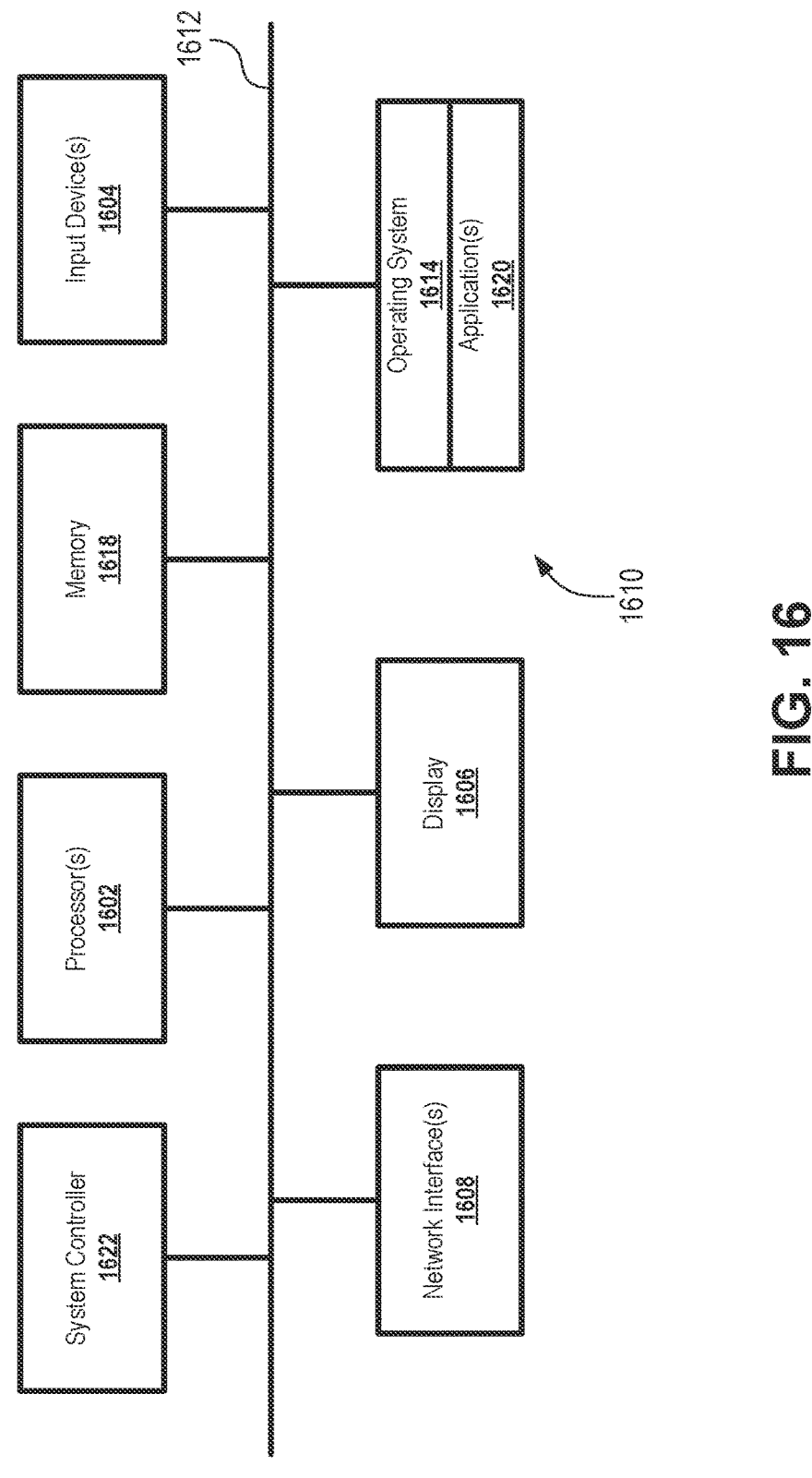
FIG. 16 is a block diagram depicting an example system architecture for implementing certain features and processes of the present disclosure.

FIG. 16 is a block diagram of an example system architecture 1600 for implementing features and processes of the present disclosure, such as those presented with reference to FIGS. 1-14. The architecture 1600 can be used to implement any suitable computing device (e.g., a server, workstation, tablet, or other such device) for practicing the various features and processes of the present disclosure. The architecture 1600 can be implemented on any electronic device that runs software applications derived from compiled instructions, including without limitation personal computers, servers, smart phones, electronic tablets, game consoles, email devices, and the like. In some implementations, the architecture 1600 can include one or more processors 1602, one or more input devices 1604, one or more display devices 1606, one or more network interfaces 1608, and one or more computer-readable mediums 1610. Each of these components can be coupled by bus 1612.

In some cases, system architecture 1600 can be incorporated into a computing system capable of performing MPI scans, such as a computing system used to control a scanner. In some cases, system architecture 1600 can be incorporated into a workstation computer used primarily for viewing and interpreting results of an MPI scan. In some cases, system architecture 1600 can be incorporated into a computer system used to train deep learning models, such as a computer system optimized for the training of deep neural networks.

Display device 1606 can be any known display technology, including but not limited to display devices using Liquid Crystal Display (LCD) or Light Emitting Diode (LED) technology. Processor(s) 1602 can use any known processor technology, including but not limited to graphics processors and multi-core processors. Input device 1604 can be any known input device technology, including but not limited to a keyboard (including a virtual keyboard), mouse, track ball, and touch-sensitive pad or display. Bus 1612 can be any known internal or external bus technology, including but not limited to ISA, EISA, PCI, PCI Express, NuBus, USB, Serial ATA or FireWire.

Computer-readable medium 1610 can be any medium that participates in providing instructions to processor(s) 1602 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium 1610 can include various instructions for implementing operating system 1614 and applications 1620 such as computer programs. The operating system can be multi-user, multiprocessing, multitasking, multithreading, real-time and the like. The operating system 1614 performs basic tasks, including but not limited to: recognizing input from input device 1604; sending output to display device 1606; keeping track of files and directories on computer-readable medium 1610; controlling peripheral devices (e.g., disk drives, printers, etc.) which can be controlled directly or through an I/O controller; and managing traffic on bus 1612. Computer-readable medium 1610 can include various instructions for implementing firmware processes, such as a BIOS. Computer-readable medium 1610 can include various instructions for implementing any of processes described herein, including at least process 1500 of FIG. 15.

Memory 1618 can include high-speed random access memory and/or non-volatile memory, such as one or more magnetic disk storage devices, one or more optical storage devices, and/or flash memory (e.g., NAND, NOR). The memory 1618 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 1618 can store an operating system, such as Darwin, RTXC, LINUX, UNIX, OS X, WINDOWS, or an embedded operating system such as VxWorks.

System controller 1622 can be a service processor that operates independently of processor 1602. In some implementations, system controller 1622 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java, Python), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semi-conductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the invention. Thus, the breadth and scope of the present invention should not be limited by any of the above described embodiments.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: receiving input data associated with a myocardial perfusion imaging study of a patient, wherein the input data comprises a set of polar maps and patient information, wherein the set of polar maps comprises a perfusion polar map, a motion polar map, and a thickening polar map, and wherein the patient information comprises at least one selected from the set consisting of sex information, age information, and cardiac volume information; providing the input data to a deep learning model, wherein the deep learning model comprises an input layer, at least one convolution layer, at least one pooling layer, and at least one fully connected layer; generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) a probability for obstructive CAD in a right coronary artery (RCA) territory, or v) any combination of i-iv; generating an attention map in response to providing the input data to the deep learning model, wherein the attention map is indicative of regions of importance associated with the obstructive CAD scoring data; and presenting, on a display device, the obstructive CAD scoring data and the attention map.

Example 2 is the system of example(s) 1, wherein generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model.

Example 3 is the system of example(s) 1 or 2, further comprising: generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data; and presenting, on the display device, the coronary artery disease probability map.

Example 4 is the system of example(s) 1-3, wherein the deep learning model was previously trained using a first set of training data collected using a vacuum-tube-photomultiplier-based camera and a second set of training data collected using a cadmium-zinc-telluride-based camera.

Example 5 is the system of example(s) 1-4, wherein providing the input data to the deep learning model comprises: providing the set of polar maps to the input layer of the deep learning model; and providing the patient information to the at least one fully connected layer of the deep learning model.

Example 6 is the system of example(s) 5, wherein the at least one fully connected layer includes a fully connected output layer, and wherein providing the patient information to the at least one fully connected layer comprises providing the patient information to the fully connected output layer.

Example 7 is the system of example(s) 1-6, wherein providing the set of polar maps to the deep learning model comprises providing the set of polar maps without pre-defined coronary territories.

Example 8 is a computer-implemented method, comprising: receiving input data associated with a myocardial perfusion imaging study of a patient, wherein the input data comprises a set of polar maps and patient information, wherein the set of polar maps comprises a perfusion polar map, a motion polar map, and a thickening polar map, and wherein the patient information comprises at least one selected from the set consisting of sex information, age information, and cardiac volume information; providing the input data to a deep learning model, wherein the deep learning model comprises an input layer, at least one convolution layer, at least one pooling layer, and at least one fully connected layer; generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) a probability for obstructive CAD in a right coronary artery (RCA) territory, or v) any combination of i-iv; generating an attention map in response to providing the input data to the deep learning model, wherein the attention map is indicative of regions of importance associated with the obstructive CAD scoring data; presenting, on a display device, the obstructive CAD scoring data and the attention map.

Example 9 is the method of example(s) 8, wherein generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model.

Example 10 is the method of example(s) 8 or 9, further comprising generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data.

Example 11 is the method of example(s) 8-10, wherein the deep learning model was previously trained using a first set of training data collected using a vacuum-tube-photomultiplier-based camera and a second set of training data collected using a cadmium-zinc-telluride-based camera.

Example 12 is the method of example(s) 8-11, wherein providing the input data to the deep learning model comprises: providing the set of polar maps to the input layer of the deep learning model; and providing the patient information to the at least one fully connected layer of the deep learning model.

Example 13 is the method of example(s) 12, wherein the at least one fully connected layer includes a fully connected output layer, and wherein providing the patient information to the at least one fully connected layer comprises providing the patient information to the fully connected output layer.

Example 14 is the method of example(s) 8-13, wherein providing the set of polar maps to the deep learning model comprises providing the set of polar maps without pre-defined coronary territories.

Example 15 is a computer-program product tangibly embodied in a non-transitory machine-readable storage medium, including instructions configured to cause a data processing apparatus to perform operations including: receiving input data associated with a myocardial perfusion imaging study of a patient, wherein the input data comprises a set of polar maps and patient information, wherein the set of polar maps comprises a perfusion polar map, a motion polar map, and a thickening polar map, and wherein the patient information comprises at least one selected form the set consisting of sex information, age information, and cardiac volume information; providing the input data to a deep learning model, wherein the deep learning model comprises an input layer, at least one convolution layer, at least one pooling layer, and at least one fully connected layer; generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) a probability for obstructive CAD in a right coronary artery (RCA) territory, or v) any combination of i-iv; generating an attention map in response to providing the input data to the deep learning model, wherein the attention map is indicative of regions of importance associated with the obstructive CAD scoring data; presenting, on a display device, the obstructive CAD scoring data and the attention map.

Example 16 is the computer-program product of example(s) 15, wherein generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model.

Example 17 is the computer-program product of example(s) 15 or 16, further comprising generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data.

Example 18 is the computer-program product of example(s) 15-17, wherein the deep learning model was previously trained using a first set of training data collected using a vacuum-tube-photomultiplier-based camera and a second set of training data collected using a cadmium-zinc-telluride-based camera.

Example 19 is the computer-program product of example(s) 15-18, wherein providing the input data to the deep learning model comprises: providing the set of polar maps to the input layer of the deep learning model; and providing the patient information to the at least one fully connected layer of the deep learning model.

Example 20 is the computer-program product of example (s) 19, wherein the at least one fully connected layer includes a fully connected output layer, and wherein providing the patient information to the at least one fully connected layer comprises providing the patient information to the fully connected output layer.

Example 21 is the computer-program product of example (s) 15-20, wherein providing the set of polar maps to the deep learning model comprises providing the set of polar maps without pre-defined coronary territories.

What is claimed is:

1. A system for detecting coronary obstructions, comprising:

one or more data processors; and a non-transitory computer-readable storage medium containing instructions which, when executed on the one or more data processors, cause the one or more data processors to perform operations including:

creating a first set of training data associated with a myocardial perfusion imaging study comprising data collected using a first type of camera and a second set of training data associated with a myocardial perfusion imaging study collected using a second type of camera wherein the second type of camera is a different type of camera than the first type of camera;

training a deep learning model using the first set of training data and the second set of training data, wherein the deep learning model comprises an input layer, at least one convolution layer, at least one pooling layer, and at least one fully connected layer;

receiving input data associated with a myocardial perfusion imaging study of a patient, wherein the input data comprises a set of polar maps generated by a camera and patient information, wherein the set of polar maps comprises a perfusion polar map, a motion polar map, and a thickening polar map, and wherein the patient information comprises at least one selected from the set consisting of sex information, age information, and cardiac volume information;

providing the input data excluding the type of camera used to generate the set of polar maps to the deep learning model generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) and a probability for obstructive CAD in a right coronary artery (RCA) territory, or v) any combination of i-iv;

generating an attention map in response to providing the input data to the deep learning model, wherein the attention map is indicative of regions of importance associated with the obstructive CAD scoring data; and presenting, on a display device, the obstructive CAD scoring data and the attention map.

2. The system of claim 1, wherein generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model.

3. The system of claim 1, further comprising:

generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data; and presenting, on the display device, the coronary artery disease probability map.

4. The system of claim 1, wherein the first set of training data is collected using a vacuum-tube-photomultiplier-based camera and the second set of training data is collected using a cadmium-zinc-telluride-based camera.

5. The system of claim 1, wherein providing the input data to the deep learning model comprises:

providing the set of polar maps to the input layer of the deep learning model; and providing the patient information to the at least one fully connected layer of the deep learning model.

6. The system of claim 5, wherein the at least one fully connected layer includes a fully connected output layer, and wherein providing the patient information to the at least one fully connected layer comprises providing the patient information to the fully connected output layer.

7. The system of claim 1, wherein providing the set of polar maps to the deep learning model comprises providing the set of polar maps without pre-defined coronary territories.

8. The system of claim 1, further comprising a scanner coupled to the one or more processors for performing a myocardial imaging study, the scanner comprising a scanner camera wherein the set of polar maps comprise the myocardial imaging study and is generated by the scanner camera.

9. The system of claim 1, wherein the attention map further comprises:

a polar map from the set of polar maps; and a coarse localization map overlayed onto the polar map from the set of polar maps, wherein the coarse localization map identifies regions of the polar maps from the set of polar maps contributing to at least one of the probability for obstructive CAD in the LAD territory, the probability for obstructive CAD in the LCx territory, and the probability for obstructive CAD in the RCA territory.

10. A computer-implemented method for detecting coronary obstructions, comprising:

creating a first set of training data associated with a myocardial perfusion imaging study comprising data collected using a first type of camera and a second set of training data associated with a myocardial perfusion imaging study collected using a second type of camera wherein the second type of camera is a different type of camera than the first type of camera;

training a deep learning model using the first set of training data and the second set of training data, wherein the deep learning model comprises an input layer, at least one convolution layer, at least one pooling layer, and at least one fully connected layer;

receiving input data associated with a myocardial perfusion imaging study of a patient, wherein the input data comprises a set of polar maps generated by a camera and patient information, wherein the set of polar maps comprises a perfusion polar map, a motion polar map, and a thickening polar map, and wherein the patient information comprises at least one selected from the set consisting of sex information, age information, and cardiac volume information;

providing the input data excluding the type of camera used to generate the set of polar maps to the deep learning model generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) and a probability for obstructive CAD in a right coronary artery (RCA) territory, or v) any combination of i-iv;

generating an attention map in response to providing the input data to the deep learning model, wherein the attention map is indicative of regions of importance associated with the obstructive CAD scoring data; and presenting, on a display device, the obstructive CAD scoring data and the attention map.

11. The method of claim 10, wherein generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model.

12. The method of claim 10, further comprising generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data.

13. The method of claim 10, wherein the first set of training data is collected using a vacuum-tube-photomultiplier-based camera and the second set of training data is collected using a cadmium-zinc-telluride-based camera.

14. The method of claim 10, wherein providing the input data to the deep learning model comprises:

providing the set of polar maps to the input layer of the deep learning model; and providing the patient information to the at least one fully connected layer of the deep learning model.

15. The method of claim 14, wherein the at least one fully connected layer includes a fully connected output layer, and wherein providing the patient information to the at least one fully connected layer comprises providing the patient information to the fully connected output layer.

16. The method of claim 10, wherein providing the set of polar maps to the deep learning model comprises providing the set of polar maps without pre-defined coronary territories.

17. A computer-program product tangibly embodied in a non-transitory machine-readable storage medium, including instructions configured to cause a data processing apparatus to perform operations including:

creating a first set of training data associated with a myocardial perfusion imaging study comprising data collected using a first type of camera and a second set of training data associated with a myocardial perfusion imaging study collected using a second type of camera wherein the second type of camera is a different type of camera than the first type of camera;

training a deep learning model using the first set of training data and the second set of training data, wherein the deep learning model comprises an input layer, at least one convolution layer, at least one pooling layer, and at least one fully connected layer;

receiving input data associated with a myocardial perfusion imaging study of a patient, wherein the input data comprises a set of polar maps generated by a camera and patient information, wherein the set of polar maps comprises a perfusion polar map, a motion polar map, and a thickening polar map, and wherein the patient information comprises at least one selected from the set consisting of sex information, age information, and cardiac volume information;

providing the input data excluding the type of camera used to generate the set of polar maps to the deep learning model generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) and a probability for obstructive CAD in a right coronary artery (RCA) territory, or v) any combination of i-iv;

generating an attention map in response to providing the input data to the deep learning model, wherein the attention map is indicative of regions of importance associated with the obstructive CAD scoring data; and presenting, on a display device, the obstructive CAD scoring data and the attention map.

18. The computer-program product of claim 17, wherein generating the attention map comprises applying gradients of a predicted vessel to a final convolution layer of the at least one convolution layer to produce the attention map, wherein the regions of importance are indicative of regions of one or more polar maps of the set of polar maps with high informational weight in the deep learning model.

19. The computer-program product of claim 17, further comprising generating a coronary artery disease probability map based on the attention map, the coronary artery disease probability map comprising a set of segments indicative of segments of a left ventricle, wherein generating the coronary artery disease probability map comprises determining severity measurements for each segment of the set of segments using the attention map and the obstructive CAD scoring data.

20. The computer-program product of claim 17, wherein the first set of training data is collected using a vacuum-tube-photomultiplier-based camera and the second set of training data is collected using a cadmium-zinc-telluride-based camera.

21. The computer-program product of claim 17, wherein providing the input data to the deep learning model comprises:

providing the set of polar maps to the input layer of the deep learning model; and providing the patient information to the at least one fully connected layer of the deep learning model.

22. The computer-program product of claim 21, wherein the at least one fully connected layer includes a fully connected output layer, and wherein providing the patient information to the at least one fully connected layer comprises providing the patient information to the fully connected output layer.

23. The computer-program product of claim 17, wherein providing the set of polar maps to the deep learning model comprises providing the set of polar maps without predefined coronary territories.

24. A method for treating obstructive coronary artery disease (CAD), comprising:

creating a first set of training data associated with a myocardial perfusion imaging study comprising data collected using a first type of camera and a second set of training data associated with a myocardial perfusion imaging study collected using a second type of camera wherein the second type of camera is a different type of camera than the first type of camera;

training a deep learning model using the first set of training data and the second set of training data, wherein the deep learning model comprises an input layer, at least one convolution layer, at least one pooling layer, and at least one fully connected layer;

receiving input data associated with a myocardial perfusion imaging study of a patient, wherein the input data comprises a set of polar maps generated by a camera and patient information, wherein the set of polar maps comprises a perfusion polar map, a motion polar map, and a thickening polar map, and wherein the patient information comprises at least one selected from the set consisting of sex information, age information, and cardiac volume information;

providing the input data excluding the type of camera used to generate the set of polar maps to the deep learning model generating obstructive coronary artery disease (CAD) scoring data in response to providing the input data to the deep learning model, wherein the obstructive CAD scoring data is indicative of i) a general probability for obstructive CAD, ii) a probability for obstructive CAD in a left anterior descending artery (LAD) territory, iii) a probability for obstructive CAD in a left circumflex artery (LCx) territory, iv) and a probability for obstructive CAD in a right coronary artery (RCA) territory, or v) any combination of i-iv;

generating an attention map in response to providing the input data to the deep learning model, wherein the attention map is indicative of regions of importance associated with the obstructive CAD scoring data;

presenting, on a display device, the obstructive CAD scoring data and the attention map;

applying a treatment for obstructive CAD based on the CAD scoring data.

* * * * *